United States Patent [19]
Yang et al.

[11] Patent Number: 5,614,378
[45] Date of Patent: Mar. 25, 1997

[54] PHOTOBIOREACTORS AND CLOSED ECOLOGICAL LIFE SUPPORT SYSTEMS AND ARTIFIFICIAL LUNGS CONTAINING THE SAME

[75] Inventors: Victor C. Yang; Robert H. Bartlett; Bernhard O. Palsson, all of Ann Arbor, Mich.; Minoo Javanmardian, Naperville, Ill.

[73] Assignee: The Regents of the University of Michigan, Ann Arbor, Mich.

[21] Appl. No.: 412,598

[22] Filed: Dec. 9, 1994

Related U.S. Application Data

[63] Continuation of Ser. No. 955,760, filed as PCT/US91/04493 Jun. 28, 1991, which is a continuation-in-part of Ser. No. 545,192, Jun. 28, 1990, abandoned.

[51] Int. Cl.$^6$ .............................. C12M 1/00; C12N 1/12
[52] U.S. Cl. .................... 435/41; 435/257.1; 435/292.1; 435/293.1; 47/1.4; 422/45; 422/48
[58] Field of Search ........................... 435/41, 71.2, 101, 435/106, 168, 173, 257.1, 257.3, 284, 287, 313, 946, 173.1, 173.8, 289.1, 292.1, 293.1, 293.2, 297.2, 257.6, 297.4, 257.4, 257.5; 47/1.4; 422/45, 48; 604/4-6; 261/DIG. 28

[56] References Cited

U.S. PATENT DOCUMENTS

| | | | |
|---|---|---|---|
| 3,186,917 | 6/1965 | Gerhardt et al. | 435/311 |
| 3,934,369 | 1/1976 | Rebeiz . | |
| 3,958,364 | 5/1976 | Schenck et al. | 435/101 |
| 4,306,018 | 12/1981 | Kirkpatrick . | |
| 4,390,624 | 6/1983 | Leavitt . | |
| 4,914,858 | 4/1990 | Nijssen et al. | 47/58 |
| 4,952,511 | 8/1990 | Radmer . | |
| 4,970,166 | 11/1990 | Mori . | |
| 5,012,609 | 5/1991 | Ignatius et al. | 47/58 |

FOREIGN PATENT DOCUMENTS

| | | | |
|---|---|---|---|
| 58-51888 | 3/1983 | Japan | 435/257.1 |
| 1063023 | 3/1989 | Japan . | |
| 2192195 | 1/1988 | United Kingdom . | |

OTHER PUBLICATIONS

Palsson et al. "Development of a Photo-Bioreactor and Green cell lines for CELSS" CAMRSS Final Report (Jun. 1989) pp. 1–33.

*Primary Examiner*—William H. Beisner
*Attorney, Agent, or Firm*—Oblon, Spivak, McClelland, Maier & Neustadt, P.C.

[57] ABSTRACT

A photobioreactor system for efficient oxygen production for a closed ecological life support system (CELSS) is disclosed. Special features of this system include, e.g., the optical transmission system, uniform light distribution, continuous cycling of cells, gravity independent gas-exchange, and an ultrafiltration unit. The fiber optic based optical transmission system illuminates the reactor internally and includes a light source which is external to the reactor, preventing heat generation problems. Uniform light distribution is achieved throughout the reactor without interfering with the turbulent regime inside. The ultrafiltration unit exchanges spent with fresh media and its use results in very high cell densities, up to $10^9$ cells/ml for *Chlorella vulgaris*. The prototype photobioreactor system may be operated in a batch and continuous mode for prolonged periods of time. The photobioreactor may be used to convert $CO_2$ to oxygen in an artificial lung.

20 Claims, 12 Drawing Sheets

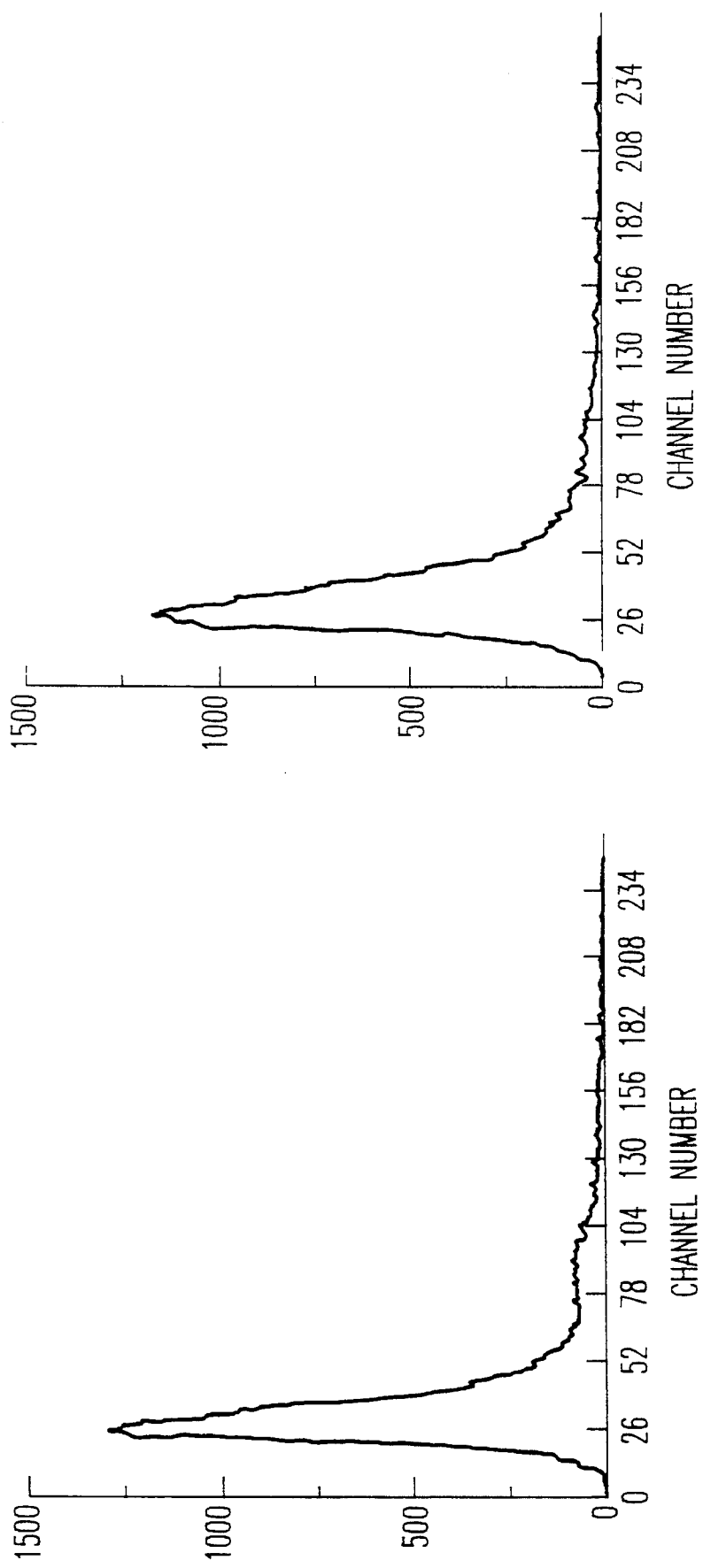

PHOTOBIOREACTORS AND CLOSED ECOLOGICAL LIFE SUPPORT SYSTEMS AND ARTIFIFICIAL LUNGS CONTAINING THE SAME

This application is a Continuation of application Ser. No. 07/955,760, filed on Feb. 18, 1993, now abandoned, which was filed as a continuation International application number PCT/US91/04493 on Jun. 28, 1991, which was a Continuation in Part of application Ser. No. 07/545,192, filed on Jun. 28, 1990, now abandoned.

TECHNICAL FIELD

The present invention relates to photobioreactors; closed ecological life support systems, artificial lungs, and apparatus for preparing oxygen from carbon dioxide, comprising such photobioreactors; and processes for preparing oxygen from carbon dioxide and methods for culturing cells utilizing such photobioreactors.

BACKGROUND ART

Many cells and microorganisms require light for growth and/or production of secondary metabolites. Similarly, cells and microorganisms capable of photosynthesis require light for the fixation of carbon dioxide and the production of oxygen. Thus, the efficient growth of photo-autotrophic cells and the efficient production of oxygen from carbon dioxide by photosynthetic cells present the need for photobioreactors.

In addition, one of the more important challenges in achieving manned flight in space for prolonged periods of time is to have an on-line workable and efficient closed ecological life support system (CELSS) which provides oxygen, food, and water for humans and recycles wastes. Many life support systems have been designed that use algal cell cultures to produce oxygen (see, e.g., Krauss, in Life Science and Space Research, Pergamon press, Holmquist, ed., New York, pp. 13–26 (1978); Miller et al, USAF School of Aerospace Medicine, SAMTR-66-11 (1966); and Wharton et al, in Algae and Human Affairs, Lembi and Waalend, eds., Cambridge University Press, pp. 486–509 (1988)). Algal cultures are primary candidates for inclusion in a bioregenerative system because; they typically grow rapidly, have metabolism that can be controlled, produce a high ratio of edible to nonedible biomass, and have gas-exchange characteristics compatible with human requirements (see Wharton et al). Successful utilization of microalgae in a CELSS requires an energy efficient and compact photobioreactor.

The issues to be addressed in an efficient design include; optimal lighting techniques and configurations with an emphasis on lighting efficiency; gravity independent gasliquid separation; minimal heat transfer; and minimal cell adherence to the surface (Averseer et al, NASA Contractor Report, 166615 (1984)). Some of these problems such as optimal lighting techniques and selection of appropriate wavelengths have already been addressed (Mori, in Symposium on Biotechnology for Fuels and Chemicals, vol. 7, pp. 331–345 (1985)). In the bioreactor of Mori, a plurality of fiberoptic light radiators are immersed within a tank. However, the problem of keeping the cells in suspension is not addressed in this apparatus. Also, the main concern of the design of Mori is to provide light of the right quality for the culture. In the present photobioreactor, the illumination source is outside the irradiation chamber, while the illumination takes place inside the chamber.

U.S. Pat. No. 4,868,123 to Berson et al discloses an apparatus for the controlled production of microorganisms in which a group of transparent tubes are placed on an expanse of water. However, the apparatus of Berson et al relies on solar rather than artificial light sources.

For the last decade, membrane lungs have been used extensively for prolonged extracorporeal life support (ECLS), particularly for neonatal respiratory failure and cardiac or pulmonary failure in children and adults. Extracorporeal life support has also been used on occasion as a bridge for lung transplantation. The two techniques of ECLS and lung transplantation should be complementary like hemodialysis and renal transplantation. Unfortunately, immune suppression is generally considered to be contraindicated in ECLS, because of bacterial infection and a low rate of successful recovery. Even if infectious complications could be solved, prolonged ECLS is an invasive procedure and is thus used only with patients who require high pressure, high oxygen mechanical ventilation, a situation generally considered to be contraindicated in lung transplantation. Thus, in the current state of the art, a problem faces both prolonged ECLS and lung transplantation.

The solution to the problem is the implantable artificial lung. However, the concept has never been evaluated in a clinical setting and very rarely tested in the animal laboratory. The major probems are in the thrombosis/microembolism in the blood phase and water accumulation in the gas phase with the membrane lung, as well as the requirement of an external gas tank for continuous supply of a high flow of 100% oxygen. Hence, the concept of the implantable lung as a support system, or as a bridge to transplantation, is at a stalemate using the current technology.

The development of artificial lungs has progressed from filming, foaming, and bubble oxygenators to membrane lungs which simulate the alveolus. Membrane lungs may be fabricated from solid silicone "rubber" polymer or from microporous material (Kolobow T, Bowman R L: Construction and evaluation of an alveolar membrane artificial heart lung, Trans. Am. Soc. Artif. Intern. Organs, 9: 238–247, 1963). For the last decade, membrane lungs have been used extensively for prolonged extracorporeal support, particularly for newborn respiratory failure. Based largely on the safety and efficacy of membrane lungs for days or weeks of chronic support, the use of membrane lungs for cardiac surgery has steadily grown during the last decade so that now more than 60% of cardiac surgical operations are done using membrane lungs. Prolonged extracorporeal life support (ECLS) for cardiac or pulmonary failure has become standard treatment for neonatal respiratory failure and has been used in many centers for prolonged cardiac or pulmonary failure in children and adults. Survival rates are 90% for newborn infants and 50% for children and adults (Dennis C: A heart lung machine for open-heart operation: How it came about, Trans. Am. Soc. Artif. Intern, Organs 35: 767–777, 1989). Extracorporeal life support cases commonly run for more than three weeks of time without major deleterious effects (Glass P, Miller M, Short B: Morbidity for survivors of extracorporeal membrane oxygenation: Neurodevelopmental outcome at 1 year of age, Pediatrics 83: 72–78, 1989). Almost all of this experience (now totaling greater than 4500 cases) has been achieved with the solid silicone rubber SciMed Kolobow membrane lung (Stolar C J, Snedecor S S, Bartless R H: Extracorporeal membrane oxygenation and neonatal respiratory failure: Experience from the extracorporeal life support organization, J. Pedi-

*atric Surg.*, in press). Although the membrane lung may malfunction and require changing after one to two weeks, there are many examples of membrane lungs which have worked successfully for three weeks or more. The major problems with membrane lungs are thrombosis and/or microembolism in the blood phase and water accumulation in the gas phase. The thrombosis problem is generally well controlled with continuous low dose systemic heparinization (Kolobow T: Gas exchange with membrane lungs, in *Neonatal and Adult Respiratory Failure: Mechanisms and Treatment* (Gille M, Ed.) pp 89–96, Elsevier, Paris, 1989). Recently, the use of heparin bonded membrane lungs has been successfully used without heparin in the laboratory and clinical trials are currently underway (Toomasian J M, Hsu L C, Hirschl R B, Hultquist K A: Evaluation of Duraflo II heparin coating in prolonged extracorporeal membrane oxygenation, *Trans, Am. Soc. Artif. Intern. Organs* 34: 410–414, 1988). The problem of water accumulation in the gas phase can be minimized by using a high gas flow rate. Heating and humidifying the gas has been reported to decrease the water accumulation. However, this will always be a potential problem with membrane lungs of the current design (Mottaghy K, Oedekoven B, Poppel K, et al: Heparin free long-term extracorporeal circulation using bioactive surfaces, *Trans. Am. Soc. Artif. Intern. Organs* 35: 635–635, 1989).

During the last five years, lung transplantation has grown from an occasional clinical curiosity to well a established clinical investigation and application in many centers. Lung transplantation has proven to be quite successful when it is applied in stable patients, who are not acutely ill and not on mechanical ventilators. The problems limiting lung transplantation are the availability of suitable donors and the fact that infectious complications are prohibitive when the recipient patients are critically ill on mechanical ventilation. Unfortunately, many patients who might benefit from lung transplantation are in the latter category. Another problem with lung transplantation is the early pulmonary failure that can occur secondary to ischemic time, reperfusion, or other causes of capillary leakage in the recently transplanted lung. This problem could possibly be successfully managed with ECLS, but immune suppression is generally considered to be contraindicated in ECLS because of bacterial infection and a low rate of successful recovery.

Extracorporeal life support has been used on occasion as a bridge to lung transplantation and the technique is certainly feasible. The two techniques of ECLS and lung transplantation should be complementary like hemodialysis and renal transplantation. Unfortunately, unlike hemodialysis in which the patient is on the procedure only a few times a week, ECLS requires the patient to be continuously immobilized to the machine. Even if the infectious complications could be solved, prolonged extracorporeal support is labor intensive, expensive, and subject to mechanical breakdown of the pumping system, not to mention the membrane lung problems described above. In addition, ECLS is a more invasive procedure as compared to that of hemodialysis. These problems render ECLS to be used only with patients who require high pressure, high oxygen mechanical ventilation, a situation generally considered to be contraindicated in lung transplantation. The problems discussed above have been reviewed in detail in a recent article published by Bartlett, R H: Current Problems in Surgery, in: *Extracorporeal Life Support Cardiopulmonary Failure* (Wells, Jr., SA, Ed.), Vol. XXVII, No. 10, pp. 627–705, Mosby-Year Book, St. Louis, Mo. 1990.

With current technology, a relatively small artificial lung with low blood flow resistance can be placed in the left chest adjacent to the native lung with end to side vascular anastomosis to the pulmonary artery and left atrium. Technically, it is relatively simple to place such a device in experimental animals and patients with either chronic or acute pulmonary failure, leaving the native lungs in place without disturbing the anatomy at the hilum of the lung, allowing subsequent transplantation, continued support as needed with the implantable lung, then removal of the implantable device. Both in concept and practice, this procedure is simpler and less disruptive than the placement of an implantable ventricular assist device or bridging artificial heart. However, the implantable lung concept has never been evaluated in a clinical setting and very rarely tested in the animal laboratory. The reason is that the useful life of currently available membrane lungs is approximately one week. Even if artificial lungs could function successfully for three or four weeks this would not be sufficient to justify the major operation of thoracotomy and implantation. To be successful for bridging to transplantation, an implantable lung would have to function for one to six months without changing the membrane lung. Of the two problems limiting prolonged function of membrane lungs, the solution to the thrombosis problem appears to be close at hand. The combination of heparin bonded surface, platelet inhibiting drugs, and careful attention to rheologic design, makes thrombosis a rare occurrence, even in the complex extracorporeal life support systems. A more significant problem for an implantable membrane lung is the gas phase. Membrane lungs require 100% oxygen at relatively high flow rates which must be continuously supplied. This requires transcutaneous gas entry and exit lines, running the risk of infection, and requiring a continuous high flow of 100% oxygen. More importantly, the accumulation of water in the gas phase with gradual loss of membrane lung function limits the useful life of membrane lungs. Even if all the above problems could be solved, the patients would still likely be secured to the oxygen supply, require intensive care, and suffer high medical costs (e.g., the costs of labor and oxygen supply).

Thus, there remains a need for photobioreactors which can achieve the efficient growth of photo-autotrophic or mixo-trophic cells and the efficient production of oxygen from carbon dioxide. In addition, there remains a need for a practical artificial lung.

DISCLOSURE OF THE INVENTION

Accordingly, it is one object of the present invention to provide novel photobioreactors for the efficient culturing of photo-autotrophic or mixo-trophic cells.

It is another object of the invention to provide photobioreactors which permit the culturing of photoautotrophic cells at high cell densities.

It is another object of the invention to provide photobioreactors for the culturing of cells which require light for the production of secondary metabolites.

It is another object of the invention to provide photobioreactors which permit the culturing of cells which require light for the production of secondary metabolites at high cell densities.

It is another object of the invention to provide photobioreactors for the efficient culturing of photosynthetic cells.

It is another object of the invention to provide photobioreactors which permit the culturing of photosynthetic cells at high densities.

It is another object of the invention to provide photobioreactors for the efficient fixation of carbon dioxide and the production of oxygen from carbon dioxide.

It is another object of the invention to provide photobioreactors which permit the fixation of carbon dioxide and the production of oxygen from carbon dioxide to be carried out at high cell densities.

It is another object of the invention to provide an apparatus for preparing oxygen from carbon dioxide.

It is another object of the invention to provide closed ecological life support systems.

It is another object of the invention to provide a process for fixing carbon dioxide.

It is another object of the invention to provide a process for preparing oxygen from carbon dioxide.

It is another object of the invention to provide a method of culturing photo-autotrophic cells, photosynthetic cells, and/or cells which require light to produce a secondary metabolite.

It is another object of the invention to provide a method for producing a secondary metabolite.

It is another object of the present invention to provide an artificial lung.

It is another object of the present invention to provide an implantable artificial lung.

It is another object of the present invention to provide an artificial lung which exhibits a reduced tendency to cause thrombosis and microembolisms.

It is another object of the present invention to provide an artificial lung which does not suffer from the draw back of water accumulation in the gas phase.

These and other objects, which will become apparent during the course of the following detailed description, have been achieved by the discovery that photobioreactors, which comprise an irradiation chamber containing at least one light radiator such that the maximum distance between any cells in said irradiation chamber and said radiator is held within 1 mm to 20 cm, preferably 1 mm to 1 cm, permit the efficient irradiation of cells within the photobioreactor. The inventors have also discovered that such photobioreactors may be used to effect the conversion of $CO_2$ to $O_2$ in an artificial lung.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 8a–8d graphically illustrate the effect of dialysis on the DNA content and distribution of cells in the present photobioreactor by plotting the number of cells versus the channel number (which is proportional to DNA content) at the onset of dialysis (8a), 7 hours after dialysis (8b), 27 hours after dialysis (8c), and 40 hours after dialysis (8d);

BEST MODE FOR CARRYING OUT THE INVENTION

Figure 1:
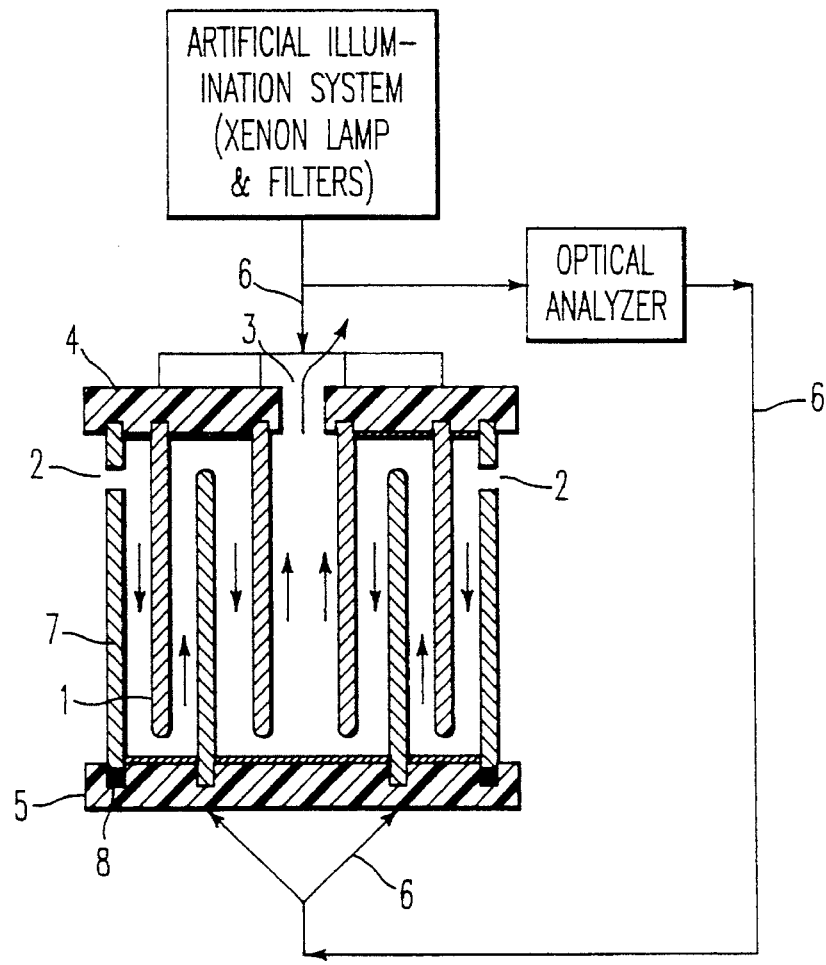
FIG. 1 is a side view of an embodiment of the present photobioreactor.

Thus, in one embodiment, the present invention is a photobioreactor in which at least one light radiator is configured such that the cells are efficiently radiated.

The requirements of the present bioreactor system is based in part on order of magnitude calculations of the light and specific surface area required for the reactor to support a human being's oxygen requirements. The volumetric oxygen production rate of a cell culture depends on three primary factors:

| Volumetric oxygen production rate | = | (Specific oxygen production rate) | (1) |
| | | X (Chlorophyll content) | (2) |
| | | X (Cell density) | (3) |

Numerical values for the three quantities (1), (2), and (3) can be estimated.

1. The specific oxygen production rate is an intrinsic property of cellular biochemistry which is directly proportional to the chlorophyll content of the cells. Representative values for this quantity are 50–400 moles oxygen produced per hour per mole of Chlorophyll (Myers et al, *Plant-Physiol.*, vol. 48, pp. 282–286 (1971)). This rate may vary with physical conditions but for practical purposes must be considered as an inherent biological constraint.

2. The chlorophyll content is a function of cell type and operating conditions, such as temperature and light intensity. It may therefore be varied by strain selection and genetic engineering. The chlorophyll content is on the order of 0.5–1.0 femto moles of chlorophyll per cell (Miller et al, *USAF School of Aerospace Medicine*, SAM-TR-69-64 (1969)).

3. The cell density is primarily a function of bioreactor design, with the illuminated surface area to volume ratio and the rate of oxygen removal being the most important design variables. Assuming a cell volume on the order 30 femtoliters/cell (typical for *Chlorella vulgaris*), the packing density of cells will be about $3 \times 10^{10}$ cells per milliliter. Therefore a density of about $10^9$ cells/ml of 3% (vol/vol) may be considered as a reasonable goal.

Using these numerical values for the three parameters, the volumetric oxygen production rate can then be estimated to be $10^{-4}$ moles oxygen generated per milliliter of culture per hour. One human being requires approximately one mole of oxygen per hour (Miller et al, *USAF School of Aerospace Medicine*, SAM-TR-66-11 (1966)), so a 10 liter unit should satisfy this need if the estimated volumetric oxygen production rate can be attained. Thus, the photobioreactor must sustain cells at these high concentrations, and maintain high growth and oxygen production rates.

Production of each oxygen molecule through photosynthetic pathway requires 8 photons of light in the blue and red region of the spectrum (Govindjee et al). Thus, the minimum light requirement is about 800 µEinstein/ml/hr, or about 40 mW/ml of light at the required wavelengths. This amount of light corresponds to about 0.4 kW of light energy per person. One of the main factors that must be considered in photobioreactor design is the light penetration distance at the required cell density. The light intensity is described in Beer's law as an exponentially decaying function of distance and cell density. For *Chlorella pyrenoidosa*, it has been shown that the penetration distance is about 1 cm at cell concentrations of about $10^8$ cells/ml (Myers, in *Algal culture From Laboratory to Pilot Plant*, Burlew, ed., Carnegie Institute of Washington, Washington, D.C. (1953)). Thus at $10^9$ cells/ml the penetration distance is about 1 mm. These calculations indicate that the required specific area for reactor is about 5–10 cm$^2$/cm$^3$, and the desired light intensity will range between 4–8 mW/cm$^2$ at the proper wavelengths. These calculations form a basis for the theoretically achievable oxygen yield.

Thus, in the present photobioreactor the optimum distance between the cells in the irradiation chamber and the light radiator is a function of cell density in the culture. Thus, for cell densities of from about $10^7$ cells/ml to about $10^9$ cells/ml the maximum distance between the radiator and any cells in the irradiation chamber is suitably from 1 mm to 20 cm, preferably 1 mm to 10 cm. Similarly, for cell densities of about $10^8$ cells/ml to about $10^9$ cells/ml, the distance is suitably 1 mm to 20 mm, preferably 1 mm to 10 mm. For cell densities above about $10^9$ cells/ml, it is preferred to maintain the maximum distance between any cells in the chamber and the radiator to at least 1 mm. In this case, the efficiency of irradiation is maintained by increasing the intensity of the irradiation.

The distance between the light radiator and the cells in the irradiation chamber may be maintained within the required distance by the use of a number of arrangements. In a simple embodiment, a single radiator may be placed lengthwise in a tubular reaction vessel, such that the distance between the chamber wall and the light radiator does not exceed the distance at which the cells and radiator may be separated. In this case, one end of the chamber can serve as an inlet port, while the other end serves as an outlet port.

In another embodiment, a substantially cylindrical light radiator is suspended from the top of the chamber and is separated from the sides and bottom of the chamber by the required distance. The chamber is equipped with at least one inlet, preferably a plurality of inlets, near the top of the sides of the chamber and an outlet at the center of the top of the chamber. In this way, when the culture is forced to flow through the irradiation chamber, the medium will flow from the inlet, down the space between the side walls of the chamber and the outer wall of the cylindrical radiator, through the space between the radiator and the chamber bottom, up the inner space of the cylindrical radiator, and out the outlet port. In this manner, good agitation and mixing of the culture may be obtained without the use of a separate agitation device, but rather by just controlling the flow rate of the culture by adjusting the pump(s) which circulates the culture.

Alternatively, the radiator may be attached to the chamber bottom, rather than the chamber top. In this case, the inlet(s) would suitably be located near the bottom of the chamber wall and the outlet would be located at the center of the chamber bottom. In another embodiment, the inlet is located at the center of the chamber top (bottom) and the outlet(s) is located near the top (bottom) of the chamber wall.

The light radiator utilized in the present photobioreactor may be of any material which is compatible with the culture, while allowing the transmission of light without absorbing it. Suitable materials for the light radiator include, but are not limited to acrylic, glass, or any material which is transparent. It is preferred that the light radiator be made of acrylic.

In the case of a substantially cylindrical light radiator, it has been found that good results are achieved with a radiator of a thickness of from 1/16 to 1 inch, preferably from 1/8 to 1/2 inch, most preferably about 1/4 inch. These radiators may be composed of two or more annuli of about 1/8 inch thickness.

These cylinders form the center of the light radiators. They are comprised of two annuli, one inserted in the other. Preferably, there are wedge-shaped cuts around (not lengthwise) the inner surface of the outer annuli and outer surface of the inner annuli, which allow light to escape evenly along the length to increase the illumination available to the algae in suspension. The dimensions of the wedgeshaped cuts are suitably 0.01 mm to 5 mm deep, at a density of 5–10 cuts/cm, or preferably 0.1 mm to 1 mm deep, at a density of about 3 cuts/cm. Preferably, the depth of the cuts increase along the length of the radiator away from its attachment. Since the rough surfaces are not in contact with the algae, clogging of the light openings with microalgae is prevented.

A preferred embodiment of the irradiation chamber is shown in FIG. 1. In this embodiment, there are three substantially cylindrical radiators (1) which are alternately attached to the bottom or the top of the reactor to ensure good agitation results from flow of the culture from the inlet (2) to the outlet (3). Both the top (4) and the bottom (5) of the chamber, as well as the radiators (1) are composed of acrylic. In this way, the light source may be connected to the top (4) and the bottom (5) of the chamber via fiber optic cables (6), and the light will travel through the top (4) and bottom (5) to the radiators (1). Thus, the fiber optic cables (6) need not be directly connected to the radiators (1). The bottom (5) of the chamber is sealed to the side wall (7) by the use of a rubber o-ring (8).

Such an arrangement provides the advantage of isolating the light source at a distance from the irradiation chamber, which obviates the problem of dissipating the waste heat of the light source from the chamber. Additionally, since the fiber optic cables are attached to the outside of the chamber, the chamber may be conveniently disconnected from the optical network without unsealing.

Figure 2:
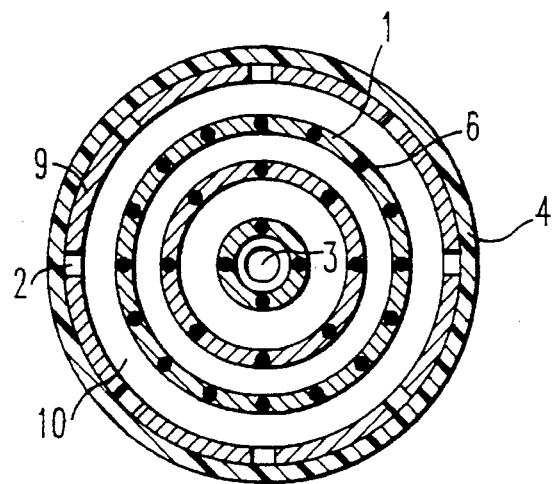
FIG. 2 is a top view of an embodiment of the present photobioreactor.

FIG. 2 provides a top view of a similar embodiment of the irradiation chamber, with two, rather than three, radiators (1). Again, the outlet (3) is located at the center of the top (4) of which only the outer edge portion is shown. The sidewall is coated with a reflective surface (9), and the placement of the fiber optic cables (6) directly above the radiators (1) is clearly shown.

In the embodiment shown in FIG. 2, there are eight inlets (2). In general, the number of inlets is adjusted to ensure adequate agitation upon flow of the culture (10) and uniform distribution of the culture. Thus, the inlets are suitably spaced around the chamber wall at a distance of 10 to 50%, preferably 30 to 40% of the diameter of the chamber wall. For the same reason, the inlets preferably have a diameter of 1/16" to 1/8" in the case of a flow rate of about 2–3 liter/min.

By increasing the number of light radiators, it is possible to increase the size and capacity of the chamber. Thus, it is preferred that the chamber possess at least two radiators, and it is particularly preferred that the chamber possess at least three radiators.

In general, to ensure good agitation, the innermost radiator will be attached to the surface (top or bottom) where the outlet port is located and the inlet port(s) will be located near the surface (top or bottom) to which the outermost radiator is attached.

Any conventional light source may be used with the present photobioreactor. In general, light of wavelengths 400 to 700 run will be required and thus, the light source is required to emit such wavelengths. It has been found that satisfactory results have been achieved with a 400 or 1000 W Xenon lamp, although other conventional sources may be utilized. Regardless of the source, appropriate conventional filters may be utilized to eliminate undesired wavelengths, such as ultraviolet radiation and a portion of the infrared radiation.

As noted above, one feature of the present invention is the isolation of the light source outside of the irradiation chamber. In this way, the waste heat of the light source poses no problem in the chamber. To achieve this end, the light must be transmitted from the light source to the chamber. Although any conventional light transmission system may be utilized, good results have been achieved by the use of fiber optic cables to transmit the light from the light source to the chamber. Thus, the light emitted from the source may be focused by appropriate conventional lenses and transmitted via the fiber optic cables.

Particularly good results have been achieved with a light transmission system in which bundles of 100 of a randomized mix of fibers optic cables, 36 inches long, having an angle of 8000 epoxy at light source, fitted with stainless steel end fittings and PVC sheathing (fiber size: 0.002 inch, bundle diameter: 0.093 inch) are spaced at a minimum distance of 1.5 mm on the top and bottom surfaces of the irradiation chamber, and the total bundle diameter at the light source is 0.96 inches.

Each fiber optic bundle has a diameter of 1/8" at the chamber. The individual fiber bundles are connected to the top and/or bottom part of the chamber through separately machined acrylic surfaces, with the appropriate number of ports of matching diameter. In this fashion the bundles fit into the light transmission device, illuminating the light radiators from the top and/or bottom surfaces of the chamber. Thus, the fiber optic bundles are suitably spaced at a distance of from 1 mm to 10 mm, preferably 1 mm to 5 mm, along the top and/or bottom surfaces of the chamber.

Alternatively, the light may be supplied to the irradiation chamber via light emitting diodes.

In the case where the present photoreactor is used to culture cells which produce and/or consume a gas, such as, e.g., photosynthetic cells which consume carbon dioxide and produce oxygen, it is preferred that the photobioreactor further comprise a gas exchange unit for, e.g., providing an adequate dissolution rate of carbon dioxide in the culture medium and ensuring an adequate stripping rate of oxygen gas. Although the gas exchange unit may be contained within the irradiation chamber of the reactor, such an arrangement can interfere with the uniform irradiation of the cells, and it is preferred that the unit be located outside the irradiation chamber. Locating the gas exchange unit outside the irradiation chamber affords the further advantages of reducing reliability problems during long term use and ease of construction. Thus, the mass transfer problems are preferably solved separately from those associated with the delivery of light. Such systems permit the use of removable cartridges in the event of fouling with, e.g., cultured algal mass.

Specifically for the case of stripping oxygen and adding carbon dioxide, it has been found that good results are achieved with a gas exchange device which comprises a carbon dioxide source along with the appropriate conventional valves and meters for introducing the desired amount of carbon dioxide. Oxygen may be removed simultaneously or in a separate device. A suitable device for removing oxygen and introducing $CO_2$ may be constructed of silicone tubing, although this material requires a substantial oxygen partial pressure difference across the membrane for oxygen transport. The use of microporous hydrophobic membranes drastically reduces the required oxygen partial pressure difference across the membrane and results in a very high mass transfer efficiency, which reduces the required size of the gas exchange unit. A particularly preferred device is a hollow fiber cartridge device manufactured by Hoechst Celanese model G-200/28.

Thus, the gas exchange module suitably has a surface area of 2 to 10 $m^2$/l of culture, preferably 3 to 5 $m^2$/l of culture; an effective pore size of 0.01 to 0.1 μm, preferably 0.3 to 0.5 μm; an operating pressure of 1 to 8 atm, preferably 1 to 5 atm; a temperature range of 0° C. to 50° C.; $O_2$—$CO_2$ exchange rate of 75 to 400 mmoles/hr/atm, preferably 75 to 100 mmoles/hr/atm; an efficiency of 80% to 100%; and a liquid flow rate range of 1 to 10 liters/min.

It is also preferred that the photobioreactor further comprise an ultrafiltration unit for the selective removal of waste and/or secreted products and the introduction of fresh media, to achieve high cell densities. It has been found, the removal of wastes and, in particular, protein products of the culture leads to increased cell division, higher cell densities, and, in the case of photosynthetic cells, higher oxygen production. Any conventional ultrafiltration unit may be suitably used, such as that produced by Filtron Technology Corporation (Minisette acrylic cell with NPT threaded ports). This unit is a high performance tangential flow membrane unit which is easily scaled up in size. The membrane is composed of polyethersulfone (PES) with a molecular weight cut off of 100 kD. The surface area is 0.75 $ft^2$ the retentate flow rate is 2 l/min, and the filtrate flow rate is 8 ml/min.

The use of an on-line ultrafiltration unit allows the system to achieve high cell densities as well as the separation of secreted products without removing the cells from the system. Suitably, the ultrafiltration system has a molecular weight cut off of at most 1000 kD; a surface area of at least 0.75 $ft^2$, preferably up to 7.5 $ft^2$; a retentate flow rate of at least 2 l/min, preferably at least 3.5 l/min; and a filtrate flow rate of at least 5 ml/min, preferably at least 50 ml/min.

Preferably, the photobioreactor further comprises an online data acquisition system. Thus, the pH, dissolved oxygen, and/or dissolved carbon dioxide may be measured on the inlet or outlet stream of the irradiation chamber. The concentration of gases may be measured, preferably automatically, by gas chromatography, and these values may be used to adjust the flow rate of the system or rate of nutrient/gas addition either manually or via an automatic feedback system.

Figure 3:
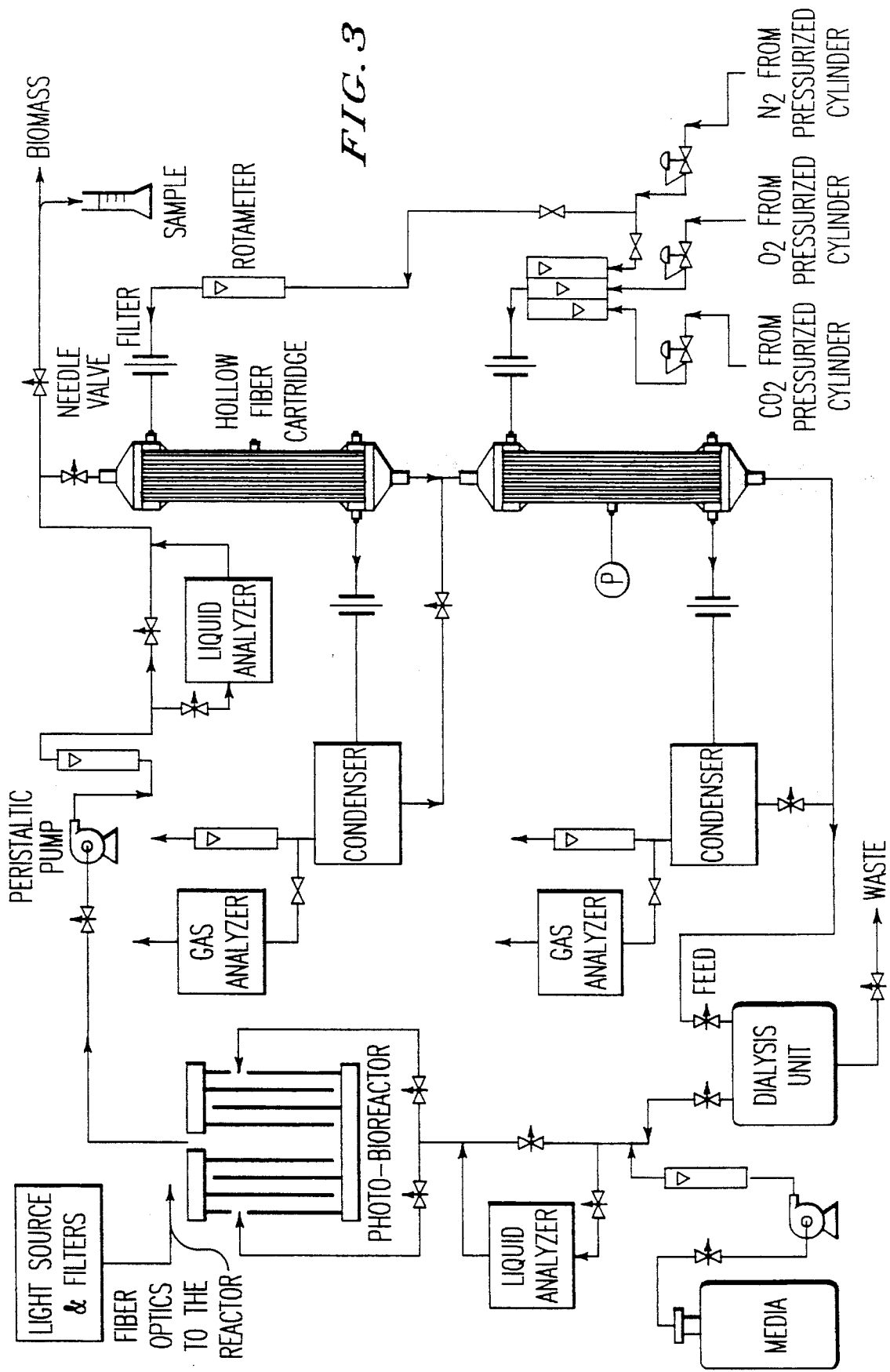
FIG. 3 illustrates schematically a preferred embodiment of the present apparatus.

A particularly preferred embodiment of the present invention is represented schematically in FIG. 3. Thus, light is transmitted from the light source to the irradiation chamber via fiber optic cables. The medium is introduced and the culture is forced to flow through the system by peristolic pumps. After the culture leaves the irradiation chamber, it flows through the gas exchange unit, represented as a hollow fiber cartridge in FIG. 3, then through the dialysis unit, before reentering the irradiation chamber. The pH, dissolved oxygen, and dissolved carbon dioxide concentrations are measured in the inlet and outlet stream of the bioreactor. These measurements, together with the gas stream analysis through an online gas chromatograph, provide a good estimation of carbon dioxide fixation rate.

In this embodiment, the photobioreactor is suitable for use as an apparatus for preparing oxygen from carbon dioxide, and thus the present invention also relates to an apparatus and method for producing oxygen from carbon dioxide, by culturing cells capable of producing oxygen from carbon dioxide in the present reactor. Suitable cells for culturing to produce oxygen from carbon dioxide are those capable of photosynthesis and include *Chlorella vulgaris, Chlorella pyrenoidosa, Scenedesmus obligus*, Euglena, Volvox, Spirolina, and any other photosynthetic prokaryotic or eucaryotic algae and higher plant cells, including photoauto- and mixotrophic cells. Such cells may be cultured in the appropriate medium, such as N-8 medium for *Chlorella vulgares*, at the appropriate temperature. The medium and temperature requirements of the various cells to be cultured are well known and discussed in *The CRC Handbook of Microalgae Mass Culture*, Ed. Amos Richard, CRC Press (1986), which is incorporated herein by reference.

The present photobioreactor may also be used as a closed ecological life support system, because of its ability to be used for the conversion of carbon dioxide to oxygen. By closed ecological life support system is meant any system which acts to supply oxygen in the absence of an external source of sufficient oxygen. Such systems have applications in, e.g., space craft, submarines, and underground and underwater dwellings. In this application the cultured cells are suitably of the genus Chlorella or Scenedesmus.

The present photobioreactor may also be used in a method to fix carbon dioxide, to produce, e.g., fuels and/or chemical feedstocks. In this application, the cultured cells are suitably, e.g., *Botryococcus braunii*.

Additionally, the photobioreactor may be used in a method for preparing secondary metabolites, by culturing cells which produce such metabolites upon irradiation. Examples of such cells and metabolites are reviewed by Metting et al, Biologically Active Compounds from Microalgae, *Enzyme Microbial. Technol.*, vol. 8, pp. 386–394 (1986), incorporated herein by reference.

The present photobioreactor may also be used in a method for the culturing of photo-autotrophic cells, examples of which include Chlorella, Scenedesmus, Chlamydononas, and Cyanobacteria.

It is to be understood that the cells which are cultured in any of the above-described methods may be those naturally occurring as either single Cell microorganisms or as part of a multicellular organism. Further, the cultured cells include those which have had their genome altered by recombinant DNA or genetic engineering techniques. This class of cells has particular importance in the method of producing secondary metabolites, in that the gene encoding for the metabolite may be introduced into the cultured cell from an external source rather than endogenously occurring in the cultured cell.

In addition, cells such as Chlamydomonas as which have been genetically altered to increase the carbon dioxide fixation rate or to increase the chlorophyll content are preferred.

Another aspect of the present invention relates to artificial lungs. The present artificial lung comprises (i) a means for converting $CO_2$ from a patient's blood stream to oxygen (the present photobioreactor) and (ii) a means for exchanging (an oxygenator) said oxygen with said $CO_2$ between said patient's blood stream and said means of converting. Any suitable blood oxygenator may be used in the present artificial lung. Blood oxygenators are disclosed in U.S. Pat. Nos. 2,854,002, 2,937,644, 3,015,331, 3,026,871, 3,075,524, 4,372,914, 3,142,296, 3,183,908, 3,729,377, 3,768,977, 4,396,584, 3,769,162, 3,769,163, 3,770,384, 3,827,860, 4,407,777, 3,853,479, 3,998,045, 4,602,987, 4,140,635, 4,612,170, 4,623,518, 4,631,053, 4,239,728, 4,749,551, 4,781,889, 4,902,476, 4,909,989, 4,923,679, 4,948,560, 4,971,836 and 4,808,378, which are incorporated herein by reference.

A number of oxygenators have been proposed and the most widely used of these are of two types: the "bubble" type in which the oxygen is introduced directly into the blood and gaseous exchange occurs during bubbling of the gas through liquid, and the "membrane" or "hollow fiber" type in which the exchange occurs through the semi-permeable wall of hollow fibers of suitable material. The second type seems to give a better guarantee from the point of view of conservation of the biochemical characteristics of the blood.

In the hollow-fiber oxygenator the blood is passed through numerous fibers (several tens of thousands) having a diameter which can vary from 100 to 300 μm and extremely porous walls (from 20 to 80%) with a pore size such as to be permeable to gases but not to liquids; the gaseous exchange of the carbon dioxide in the blood flowing inside the walls and the oxygen flowing outside them occurs through these walls. Generally, these fibers are joined into a bundle which is sealingly inserted in a cylindrical container.

The gas-exchange membranes which are currently used in the membrane type artificial lungs are of two major types; homogeneous membranes and porous membranes. As homogeneous membranes, silicone membranes are predominantly used. In contrast, porous membranes are made of various materials such as, for example, polyethylene, polypropylene, polytetrafluoroethylene, polysulfones, polyacrylonitrile, polyurethane, polyamides, polyethylene terephthalate, polybutylene terephthalate, and polycarbonate.

Taheri (U.S. Pat. No. 4,631,053) discloses an implantable oxygenator, and implantable oxygenators are preferred.

Carbonic anhydrase may also be used in facilitating the transport of carbon dioxide across membranes. Examples of publications which describe this application include Broun et al, *Biomed. Appl. Immobilized Enzymes Proteins*, 1, 401–413 (1977); Quinn et al, *Biophys. Physiol. Carbon*

*Dioxide*, Symp. 1979, 23–25 (1980). Carbonic anhydrase has also been used in combination with immobilized urease to remove urea from blood as described in Funakubo, Japanese Patent No. 82: 192,561. Membrane-bound carbonic anhydrase and other immobilized forms of this enzyme have also been disclosed in various U.S. patents including U.S. Pat. Nos. 4,092,219; 4,066,512; 4,004,979; 3,977,941; 3,954,678; 3,933,588; 3,910,780; and 3,905,923. Of particular interest is U.S. Pat. No. 3,910,780 which describes enhanced transport of carbon dioxide in a rebreather-type underwater breathing apparatus.

Carbonic anhydrase catalyzes the reversible hydration of carbon dioxide to carbonic acid. Thus, the reactions catalyzed by this enzyme are similar to those shown relating to the direct dissolution of carbon dioxide in water. However, the rate of reaction in the presence of carbonic anhydrase is extremely fast, thereby providing a rapid and efficient manner of removing carbon dioxide from fluids of all types. The fluid may be either a liquid or a gas. When carbon dioxide is being extracted from a liquid, it is preferred to contact the liquid stream with a membrane which divides the liquid stream from an aqueous solution which is in contact with the immobilized enzyme. Such an arrangement is considered to involve "contact" between the enzyme and the fluid from which carbon dioxide is being removed for the purposes of this invention. It is also possible to attach the enzyme directly to or entrap the enzyme in the membrane which separates the fluid and aqueous phases. Inclusion of carbonic anhydrase in or on the membrane allows more rapid passage of carbon dioxide across the membrane.

In a preferred embodiment of the invention, carbonic anhydrase is immobilized on a surface or entrapped within the gas permeable membrane itself. Various methods for entrapping or otherwise immobilizing carbonic anhydrase in membranes are disclosed in the prior art.

The term "carbonic anhydrase" refers to any carbon dioxide hydrating enzyme obtained from the blood or tissue of an animal or to any such enzyme which has been chemically modified while retaining its ability to hydrate carbon dioxide into carbonic acid. Preferred are carbonic anhydrase enzymes obtained from animal blood. Because of the ready availability of blood from livestock animals slaughtered for meat, such blood is a preferred source of enzymes.

Other features of the invention will become apparent in the course of the following descriptions of exemplary embodiments which are given for illustration of the invention and are not intended to be limiting thereof.

EXAMPLES

I. Photobioreactor

Apparatus

The following experiments were carried out in a prototype photobioreactor similar to that shown in FIG. 3.

The irradiation chamber had a volume of 600 ml and a specific illuminated area of 3.2 $cm^2/cm^3$. The light source was a Xenon lamp that provides 3.2 W of light in the visible portion of spectrum into the chamber. The light intensity at the illuminated surfaces is about 1 $mW/cm^2$. About 60% of this light falls into the blue and red region of the spectrum which can be utilized by the cells, resulting in about 0.6 $mW/cm^2$ of useable light.

The gas exchange device is external to the chamber, and a closed loop system is used to circulate the culture between the chamber and the gas exchange device. The circulation rate is calibrated so that the incoming stream to the chamber is low in oxygen and the exiting stream is close to saturation. The gas exchange process of the culture is carried out in hollow fiber cartridges, which can be used as a single unit, or in serial or parallel arrangements. In the serial arrangement, oxygen can be stripped off the culture in one unit under low pressure, and carbon dioxide can be dissolved in the culture in another unit under high pressure to increase the solubility. The gas supplied to the cartridge is a mixture of nitrogen, oxygen, and carbon dioxide, whose compositions can be controlled. The effluent gases from the hollow fiber cartridge flow through a condenser, trapping the water vapor prior to analysis of the gas composition. The pH, dissolved oxygen, and dissolved carbon dioxide concentrations in the inlet and outlet streams are acquired every 5 minutes by a Macintosh computer. The on-line data acquisition system provides a direct measurement of the carbon dioxide fixation, and oxygen production rates. An on-line ultrafiltration unit was used to dialyze the culture medium at a relatively high flow rate. This unit permits the selective separation of the waste and/or secreted products and exchange with fresh media.

Materials and Methods

*Chlorella vulgaris* Emerson strain, from Carolina Biological Supply was cultured in the bioreactor system in N-8 medium at a pH of 5.6. The medium consisted of (mg/lit): $Na_2HPO_4 \cdot 2H_2O$, 260; $KH_2PO_4$, 740; $CaCl_2$, 10; Fe EDTA, 10; $MgSO_4 \cdot 7H_2O$, 50; $KNO_3$, 1000; and trace elements such as $Al_2(SO_4)_3$, $MnCl_2$, $CuSO_4$, and $ZnSO_4$.

Algal cell concentration was measured with a Coulter Counter Model ZM. This system also includes a Coulter Channelizer which can measure particle size distributions. The culture was cultivated in the system with a circulation flow rate of ≈2 liters per minute. The gas composition to the cartridge was controlled by multitube flowmeters. The input gas composition to the hollow fiber was kept at 15% $O_2$, 15% $CO_2$, and 70% $N_2$ with a total flow rate of 300 ml/min. The rate of ultrafiltration was about 8 ml/min, and the molecular cut-off of the membrane was 100 kD. The light intensity inside the reactor was measured by an LI-COR light meter model LI-185 from LAMBDA Instruments Corporation which indicated an intensity of 0.6 $mW/cm^2$ of usable light inside the chamber, and the light energy provided to the chamber was about 3.2 mW.

Cell Growth

Figure 4:
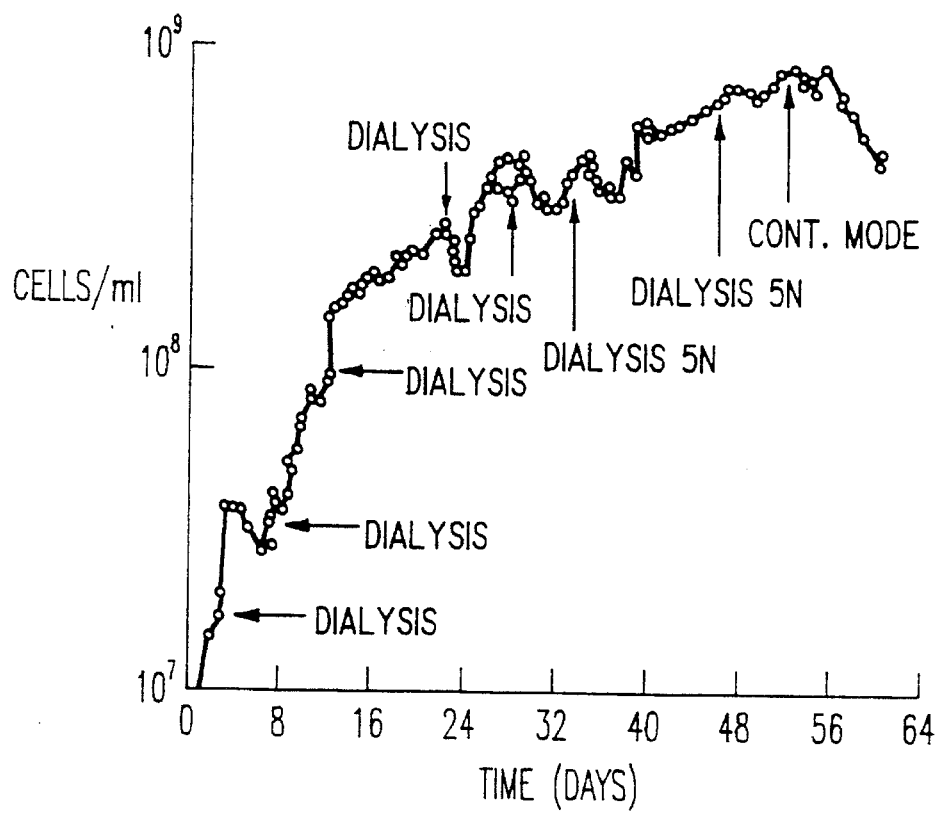
FIG. 4 graphically illustrates the growth curve of *Chlorella vulgaris* in the present photobioreactor.

*Chlorella vulgaris* inoculated at $10^7$ cells/ml in the reactor was grown up to $10^9$ cells/ml in the photobioreactor system in a batch mode, and the cell density as a function of time is presented in FIG. 4.

Oxygen Production

Figure 5:
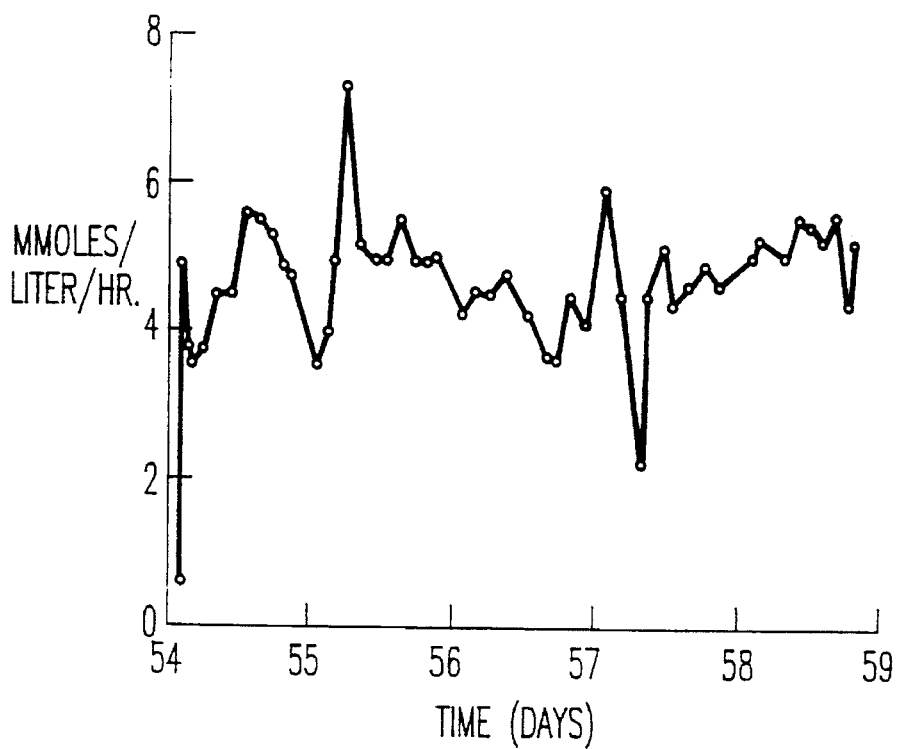
FIG. 5 graphically illustrates the oxygen production rate of *Chlorella vulgaris* in the present photobioreactor operating in the continuous mode.

The system was switched to continuous mode on day 54, with a dilution rate of 0.15 per day. The oxygen production rate under these conditions was in the range between 4–6 millimoles per liter of culture per hour (FIG. 5). This amount of oxygen corresponds to a steady state concentration of $4 \times 10^8$ cells/m, and dilution rate of 0.15/day in the system, which in turn will correspond to a 200 liter unit required to support one human being. The production rate of oxygen is close to the order of magnitude calculations based on the provided light energy (3.2 W) and specific area of the reactor (3.2 $cm^2/cm^3$).

Effect of Dialysis

Figure 6:
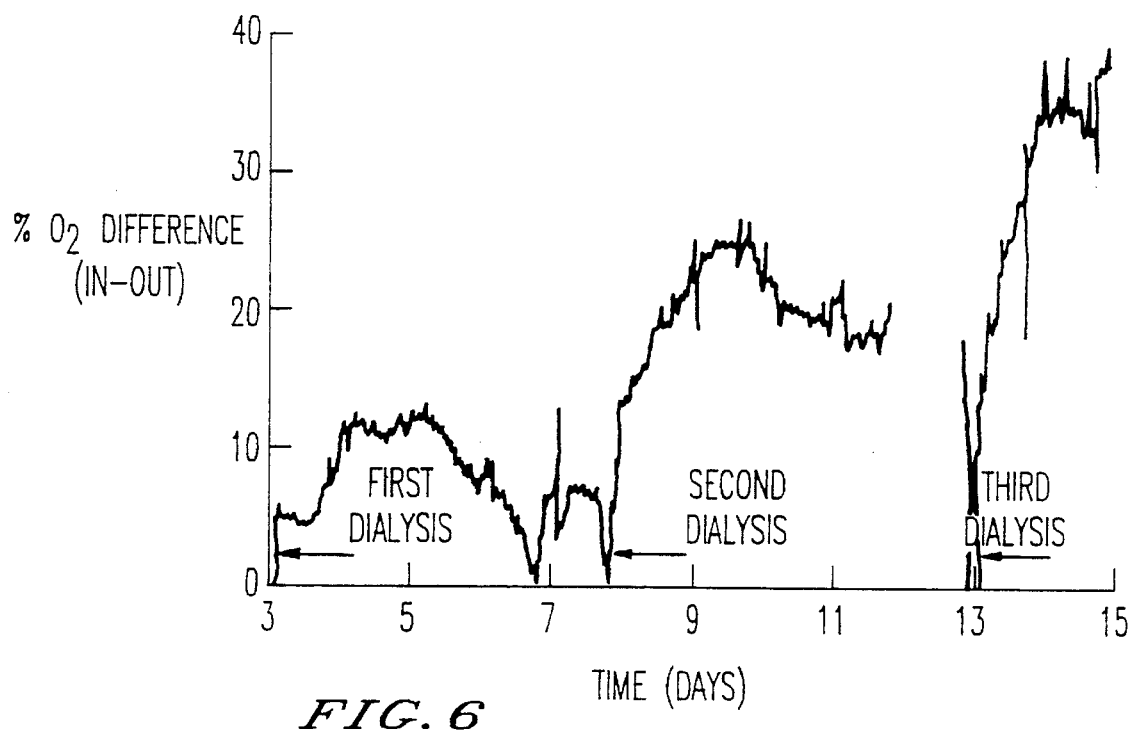
FIG. 6 graphically illustrates the effect of dialysis on the specific oxygen production rate of *Chlorella vulgaris* in the present photobioreactor.
Figure 7:
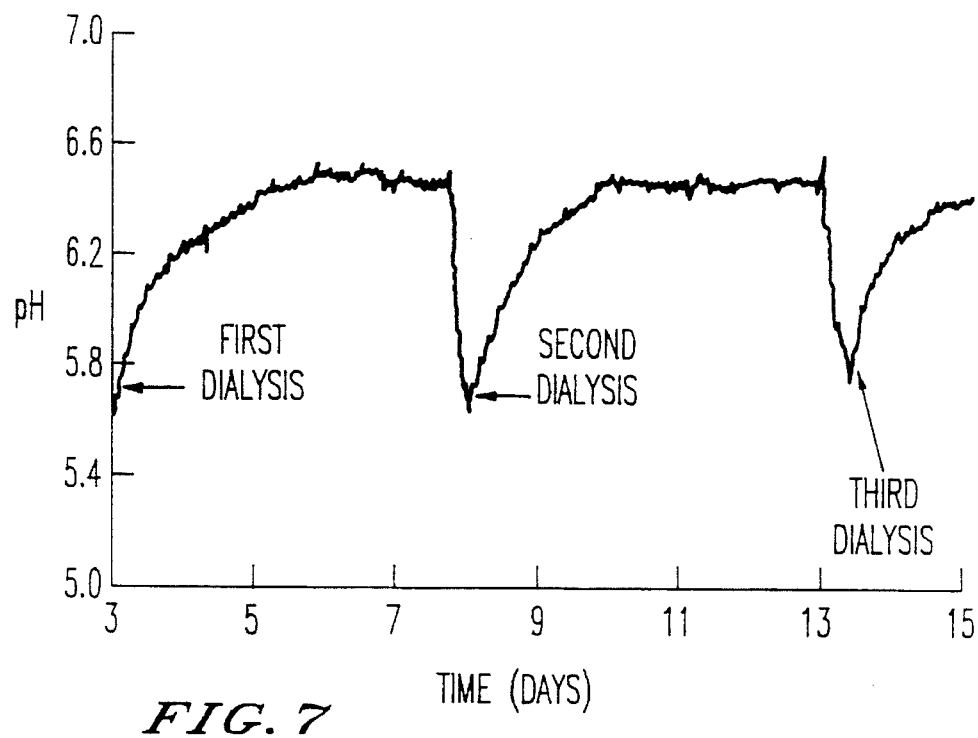
FIG. 7 graphically illustrates the effect of dialysis on the pH of a culture of *Chlorella vulgaris* in the present photobioreactor.
Figure 8A:
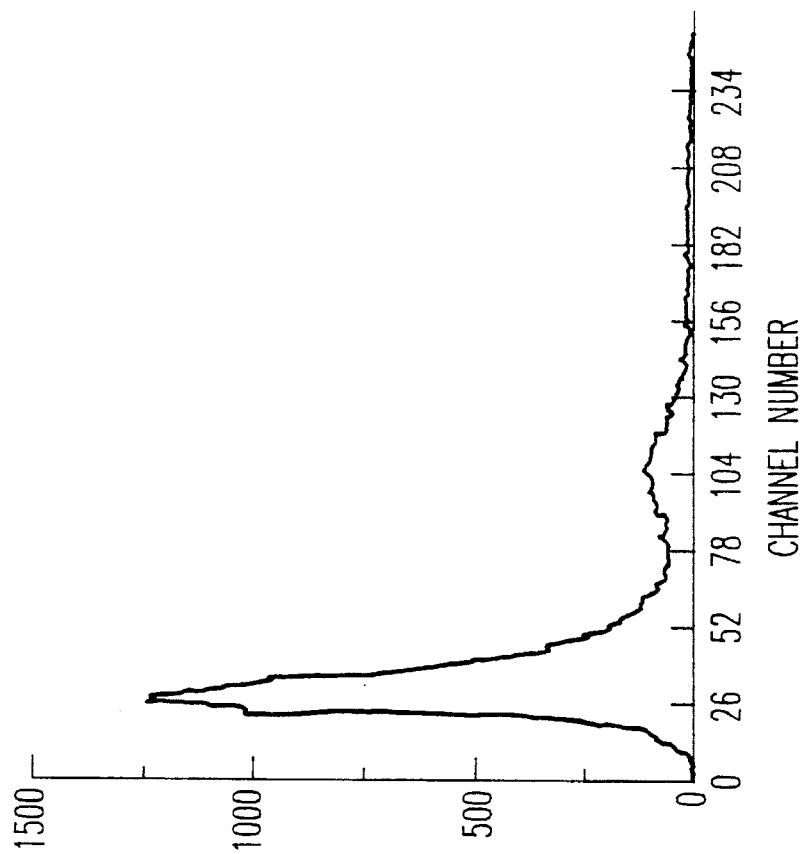
Figure 8B:
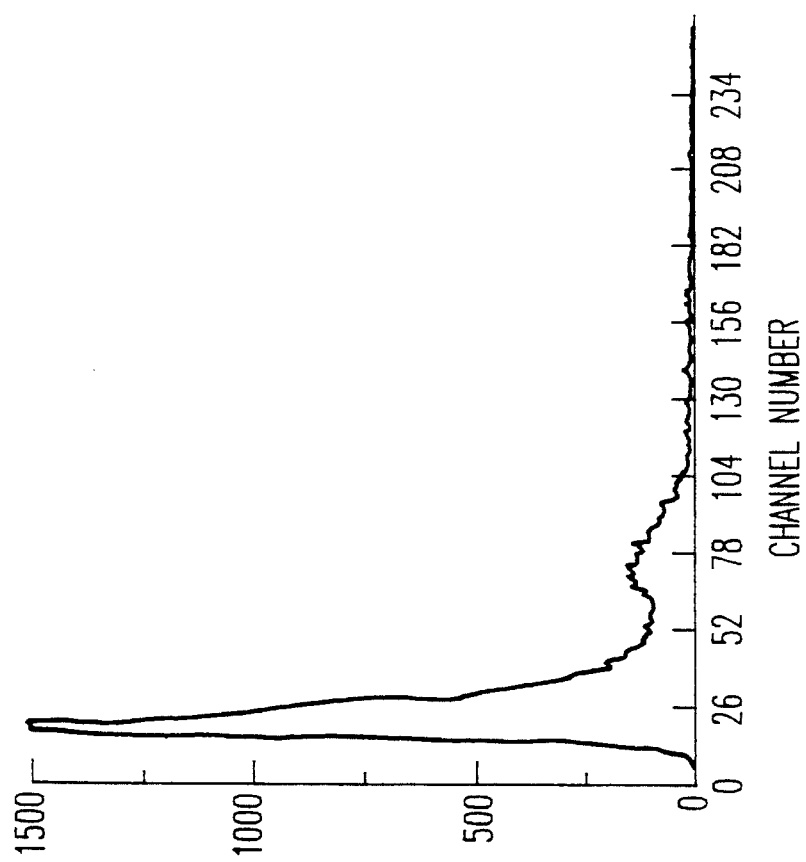

The importance of an ultrafiltration unit in achieving cell densities greater than $10^8$ cells/ml was demonstrated as follows. FIG. 6 shows that the specific oxygen production rate is increased following medium dialysis. Thus, prior to dialysis, the culture is either nutrient limited or there are secreted growth inhibitory factors that are accumulated in the culture. The nutrient limitation factor has been ruled out by dialyzing the culture against medium with high concentrations of nitrate (FIG. 4). FIG. 7 shows the effect of dialysis on the pH of the culture. The pH drops to about 5.6 which is the pH of fresh medium and rises after dialysis is stopped. The optimization and control of the pH is of significant importance in keeping the culture in a favorable environment for growth and this is an easy parameter to control once the optimum pH is identified.

FIGS. 8a–8d show flow cytometrically determined DNA histograms throughout one cycle of dialysis. Before dialysis the culture was not growing actively, and there is a peak at high DNA contents, indicating that growth probably is halted both at the division and commitment stages in the cell cycle. Following dialysis, the DNA histograms show that this peak disappears and the culture resumes its normal growth condition.

Figure 9:
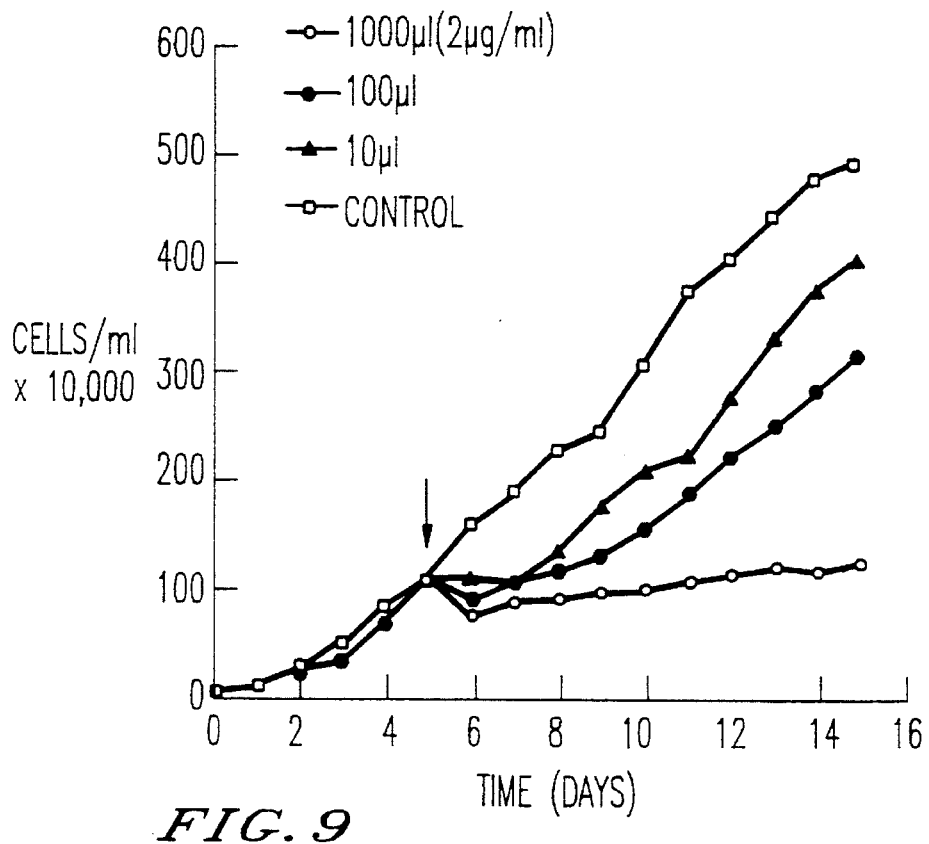
FIG. 9 graphically illustrates the relationship between cell growth and the concentration of the protein and/or secreted products removed by dialysis (↓ indicates addition of protein and/or secreted products)

Following this observation, an experiment was attempted to confirm the inhibitory effect of the secreted products from the photobioreactor at high cell concentrations. After the culture was grown to about $5\times10^8$ cells/ml, it was dialyzed by using an ultrafiltration unit against 8 liters of fresh medium. The filtrate solution was then concentrated by using freeze drying unit and then a small sample of it was used to do gel electrophoresis to confirm the existence of proteins in the culture. The results from the gel showed a total of 10 bands of proteins in the range of 1–100 k Daltons. The concentrated proteins were then used to run an experiment in four 250 ml flasks under controlled temperature and light intensity. FIG. 9 shows the effect of different concentration of secreted proteins on the growth rate of *Chlorella vulgaris*, and compares it to the control culture which has no inhibitory factors in it. FIGS. 10a–10f compare the DNA histogram of the control culture with the one that has 2 microgram/ml of the inhibitory proteins. In the controlled culture, the DNA histogram is broad and it shows that the cells are constantly going through the cycle at a constant rate. However, in the culture with inhibitory factors after the growth inhibitor was added (day 6) the DNA histogram changes, and it seems that the cells do not commit themselves to division and once the autospores are released they don't go through the cycle. Thus, at day 8 most of the cells are accumulated at the first peak (sharp peak), and there is no sign of the commitment to division (broad peak).

II. Artificial Lung

Figure 11:
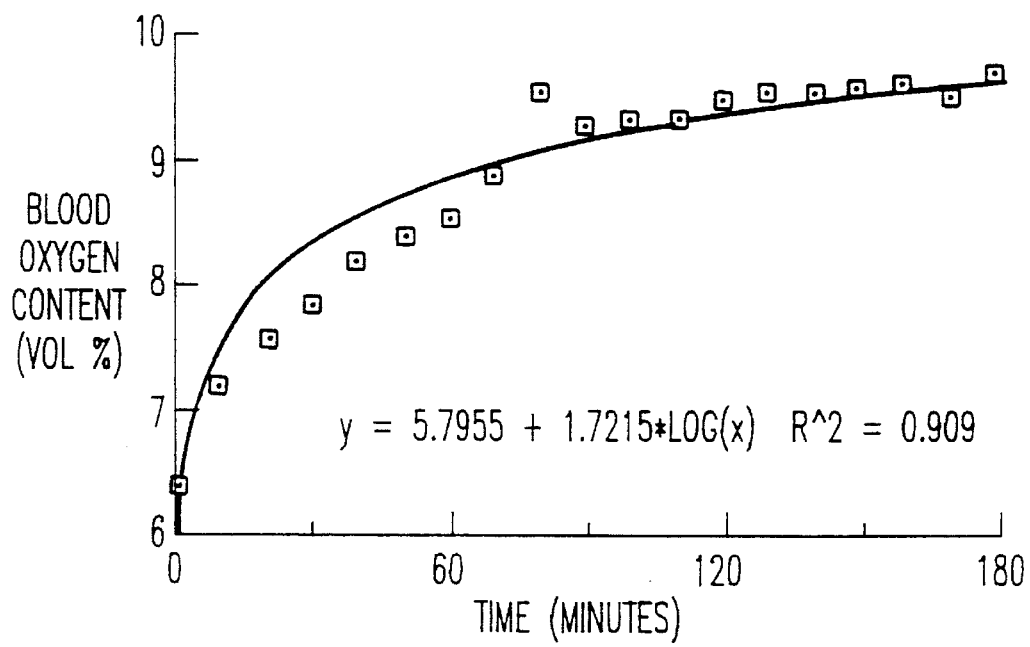
FIG. 11 graphically illustrates the results of gas exchange studies using an embodiment of the present artificial lung.
Figure 10A:
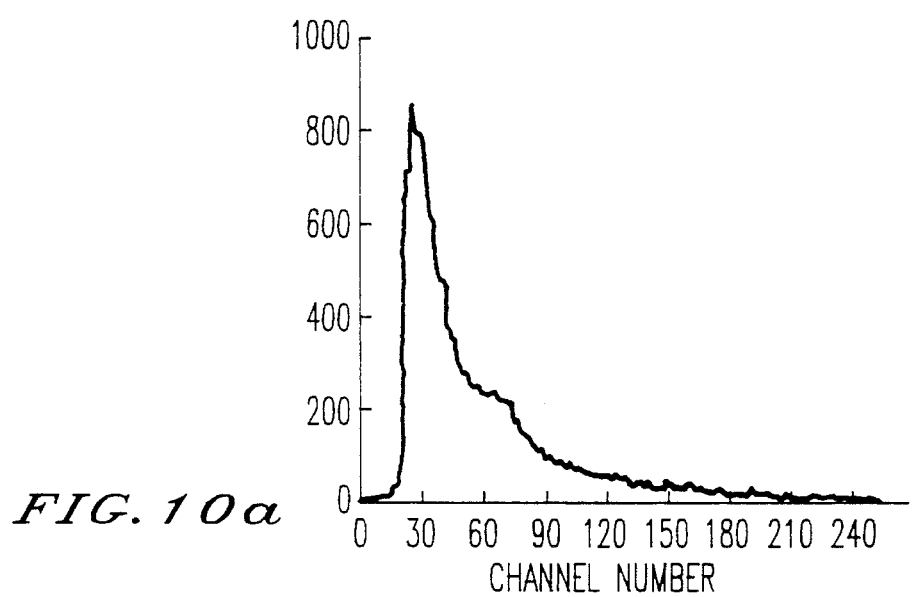
FIGS. 10a–10f graphically illustrate the effect of the presence of the protein and/or secreted products removed by dialysis on the DNA content of cells by plotting the number of cells versus the channel number (which is proportional to DNA content) 8, 9, and 10 days after culturing in the absence of the added protein (10a, 10b, and 10c, respectively) and at days 5 (protein just added), 6, and 8 in a culture in the presence of 2 μg/ml of added protein (10d, 10e, and 10f, respectively).
Figure 10B:
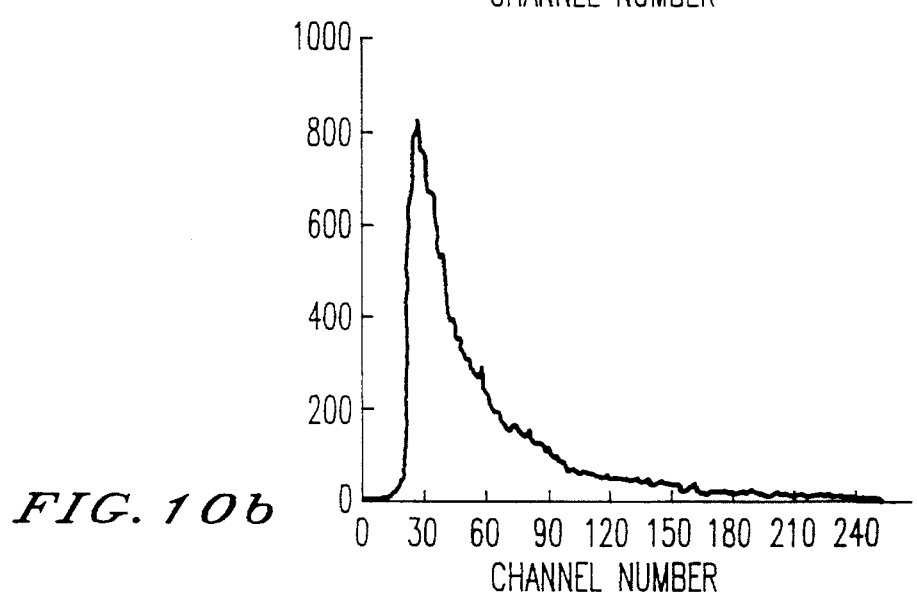
Figure 10C:
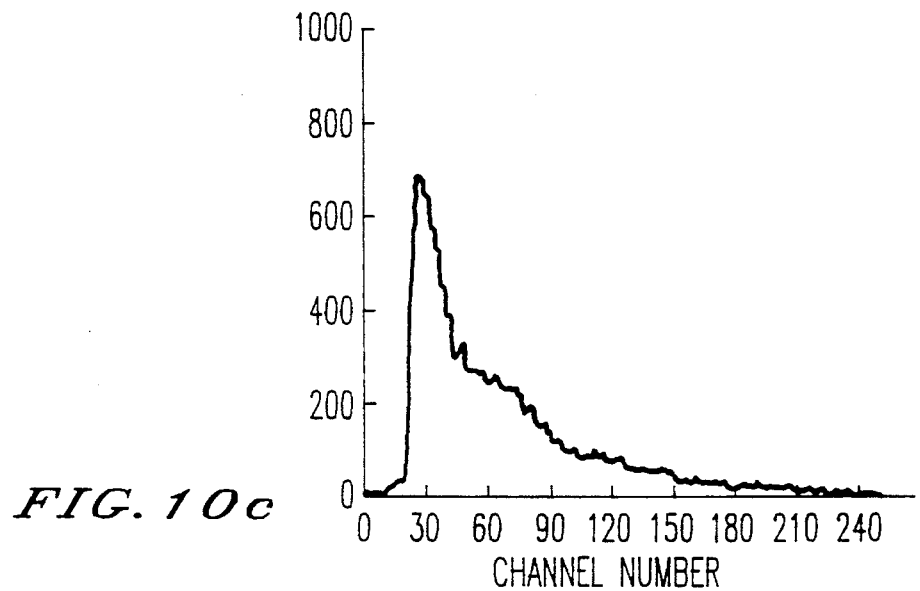
Figure 10D:
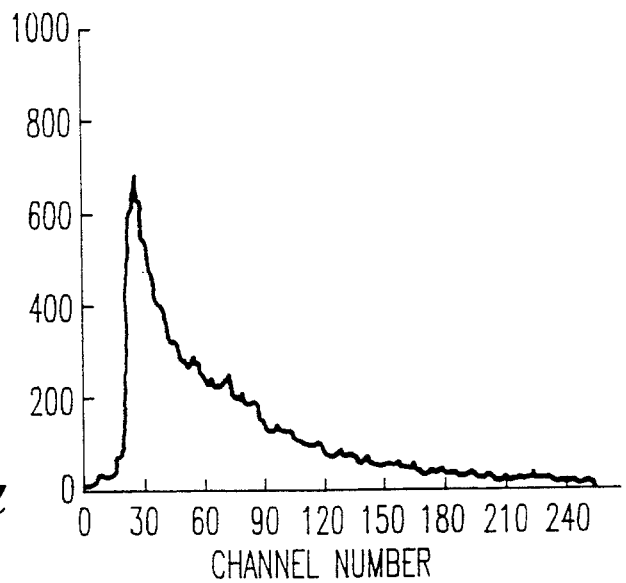
Figure 10E:
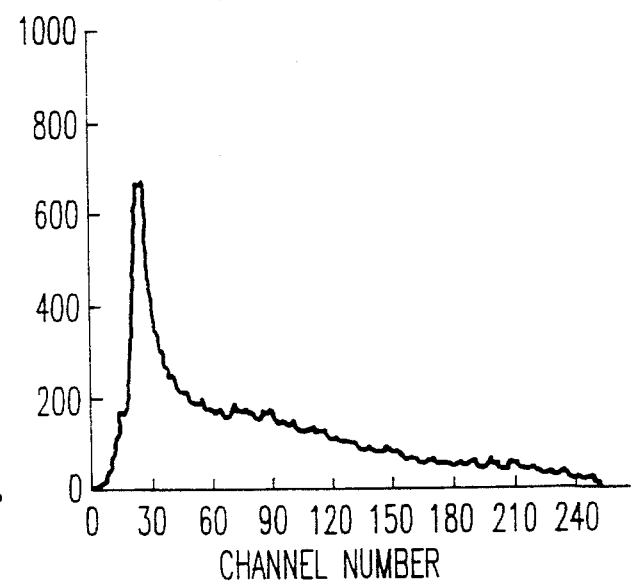
Figure 10F:
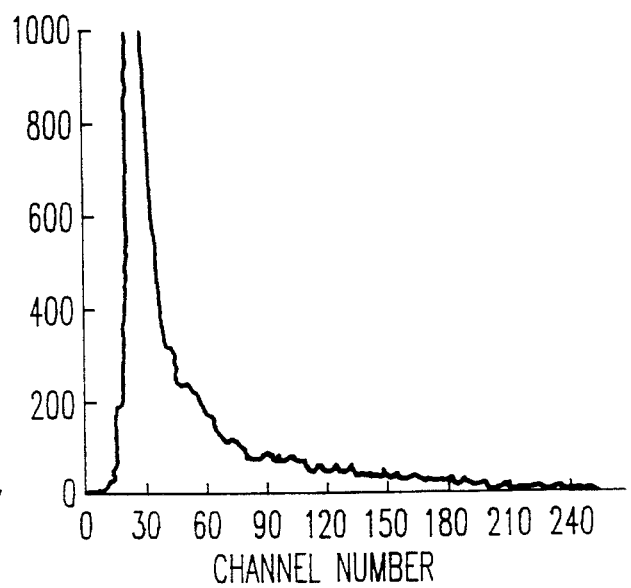

Two liters of fresh, heparinized sheep blood was normalized by a Medtronic Maxima oxygenator that achieved the $CO_2$ production and oxygen consumption of the in vivo situation. The blood was normalized by a sweep flow $FiCO_2$ (fraction of inspired carbon dioxide) of 46 torr (mmHg), and then pumped through a Bentley BOS-CM40 hollow fiber oxygenator. Algal suspension was pumped from the above-mentioned photobioreactor into the gas phase of the Bentley oxygenator in a counter-current flow. The photo-bioreactor had a total culture volume of 600 mL, a cell density of about $10^9$ cells/mL, and an oxygen production rate of approximately 45 mL $O_2$ per liter of the culture per hour. Blood gas was analyzed using the Radiometer Gas Analyzer ABL30 to assure that oxygen was generated only from the photo-bioreactor and not from the blender. Several flow rates of blood and algae perfusion were tested. The flow rate used to achieve the optimum performance was found to be 1 L/min for both the blood and algal suspension. Blood oxygen content was calculated using the equation: oxygen content= [hemoglobin (g/dL)×1.36×saturation of hemoglobin]+ [$PO_2$×0.003] (Kleiber M, *The Fire of Life*, 3rd ed., Robert Krieger Company, Malabor Fla., 1987). Saturation of the hemoglobin was measured using an IL282 Blood Cooximeter. A gradual increase in oxygen content was noted over time. The maximum oxygenation of the blood volume was accomplished in approximately 180 minutes. The oxygen produced by the photo-bioreactor appeared to cross the hollow fiber membrane and enter the blood, as evidenced by the increse in partial pressure of oxygen and the saturation of the hemoglobin. The amount of oxygen diffused into the blood phase per hour (22.4 mL/h), as estimated from FIG. 11, accounts for about 83% of the oxygen produced by the photo-bioreactor per hour (27 mL/h). It was also demonstrated by this experiment that the artificial oxygenation membrane, the volume of algae in the bioreactor, the oxygen generation rate, and the flow rates of blood and algal suspension could all be calculated to meet changing metabolic demands.

Experimental Design and Methods

Culture Selection

The choice of algae will affect algal growth reactor design and all aspects of physiology, nutrition, growth, and sensitivity to microgravity and radiation. It is very important to ensure that the algal species selected can provide the highest oxygen generation efficiency as possible because of the limited volume of culture medium available in the photo-bioreactor. In addition, since a number of blue-geen algae are know to produce toxins (Ransom R E, Nerad T A, Meier P G: Acute toxicity of some blue gree algae to the protozoan paramecium caudatum, *J. Phycol.* 14: 114–116, 1978; Carmichael W W, Jones C L A, Mahmood N A, ATheiss W C: Algal toxins and water-based diseases, *CRC Critical Reviews in Environmental Control* 15: 275–313, 1985; and Gorham P R: Toxic algae, in: Jackson D F (ed.), *Algae and Man*, pp 307–336, Plenum Press, New York, 1964), an additional facet of the selection criteria is to find algal species which will fix nitrogen and not be toxic to exposed organisms.

Past and present use of algae for close-loop ecological life support systems (CELSS) has mainly tested the unicellular green algae, *Chlorella vulgaris* and *pyrenoidosa*, out of 2000 algae species. Good results are obtained with *Chlorella vulgaris*. Additionally, there are no known toxic effects caused by Chlorella, a member of the Division Chlorophyta. Toxin-producing algae are only found in the Chrysophyta, Cyanophyta, and Pyrrhophyta (Carmichael W W, Jones C L A, Mahmood N A, ATheiss W C: Algal toxins and water-based diseases, *CRC Critical Reviews in Environmental Control* 15: 275–313, 1985). Furthermore, species of Chlorella are intercellular symbionts in many invertebrate phyla, indicating a general lack of toxicity to other organisms.

Other species of green algae (Chlorophyta) may also be appropriate for use in this context. *Serenastrum capricornutum* is easy to maintain in culture, and cell division is comparable to that of Chlorella. However, the oxygen production rate exceeds that of Chlorella (Sarsfield L J: *Properties of cadmium complexes and their effect on toxicity to a biological system*, University of Michigan Ph.D. Dissertation, 1976). Similarily, *Scemedesmus auadricauda* may also be a potential altenative. This alga is also easy to maintain, and has a growth rate and a rate of oxygen production similar to that of Selenastrum (Sarsfield L J: *Properties of cadmium complexes and their effect on toxicity to a biological system*, University of Michigan Ph.D. Dissertation, 1976).

Certain nitrogen-fixing algae belonging to the Division Cyanophyta (blue-green algae) may also be used. Not all of the Cyanophyta are toxic. Common genera which are able to fix nitrogen and have not been indicated in the literature to show toxic effects are Anabaenopsis, Aulosira, Cylindrospermum, and Tolypothrix.

Biological/Physical Constraints

The volumetric production rate of oxygen depends on three primary factors:

Volumetric oxygen production rate=(specific oxygen production rate of chlorophyll)×(chlorophyll content per cell)×(cell density)

The specific oxygen production rate is an intrinsic property of the biochemistry. Representative values for this quantity are 100–200 moles of oxygen produced per hour per mole of chlorophyll (Myers J, Graham J R: The photosynthetic unit in chlorell measured by repetitive short flashes, *Plant Physiol.* 48: 282–286, 1971). This rate may vary with conditions such as temperature, but for most practical proposes it is a quantity that is beyond control.

The chlorophyll content is a function of cell type, physiological state and gene regulation. It is therefore subject to modification through strain selection, improvement and genetic engineering. The chlorophyll content is on the order of 0.5–1 femto-mol chlorophyll per cell (Miller R L: Design and preliminary evaluation of a man-rate photosynthetic exchanger. *USAF School of Aerospace Medicine*, SAM-TR-69-64, 1969).

The cell density is primarily a function of bioreactor design, with the rate of oxygen removal and the volumetric delivery of light as the most important design variables. The volume of a Chlorella cell is about 30 femto-liters, and thus, the packing density of cell is on the order of $3 \times 10^{10}$ cells per milliliter. Thus, a cell density of $10^9$ cells per mL, or 3% (vol/vol) may be realistically aimed for.

With these typical numerical values for three parameters, one obtains a value for the volumetric oxygen production rate of $10^{-4}$ moles oxygen generated per mL per hour. A human being requires about 1 mole of oxygen per hour (Miller R L, Ward C H: Algal bioregenerative systems, in: *USAF School of Aerospace Medicine*, SAM-TR-69-64, 1969; Kleiber M., *The Fire of Life*, 3rd ed., Robert Krieger Company, Malabor Fla., 1987), and thus a 10 liter unit could supply this need. However, the bioreactor will have to be able to harbor cells at this high concentration, keep the chlorophyll content high and supply enough light per unit volume to supply the photosynthetic apparatus operating at full capacity.

Each oxygen molecule that is formed needs 8 photons of light. Thus, the minimum light that needs to be provided is about 800 uE/mL/hr, or about 40 mW/mL of light at the correct wavelengths. This amount of light corresponds to a theoretical minimum light requirement of about 0.4 kW per human being, if the spectral composition of the light matches the adsorption of the photosynthetic apparatus. The light source may not have an ideal spectral composition.

Since the light is emitted over a surface into the solution, one needs to estimate how much light-emitting surface is needed per unit culture volume. The penetration distance of light may be estimated with Beer's law (Burlew J S. *Algal Culture from Laboratory to Pilot Plant*, Carnegie Institution of Washington Publication, pp 3–28, Washington, D.C., 1953) as $$I(\chi)=I_{in}\exp(-A_\chi)=I_{in}\exp(-an_\chi)$$

where the light intensity (I) falls exponentially with distance ($\chi$) into solution. The length constant (A) is proportional to the cell density (n). For *Chlorella pyrenoidosa*, it has been shown that the penetration distance of light at 680 nm is about 1 cm at cell concentrations of $10^8$ cells/mL, so that at $10^9$ cells/mL, the penetration distance is 1 mm (Meyer J. *Algal Culture from Laboratory to Pilot Plant*, Carnegie Institution of Washington Publication, pp 37–54, Washington, D.C., 1953). Therefore, the specific area that the reactor should have is on the order of 5–10 $cm^2/cm^3$, and the desired light intensity would be on the order of 4–8 $mW/cm^2$ of light at the proper wavelength. These calculations are summerized in Table 1.

TABLE I

| Design Requirements for Bioactive, Artificial Lung Design | |
|---|---|
| PARAMETER | |
| Light Intensity | 4–8 $mW/cm^2$ |
| Specific Surface Area | 5–10 $cm^2/cm^3$ |
| Cell Density | $10^9$ cells/mL |
| Cell Growth Rate | 30–60 g/day/L |
| Culture Volume/person* | 10–20 liters |

Perfusion Chambers

Figure 12:
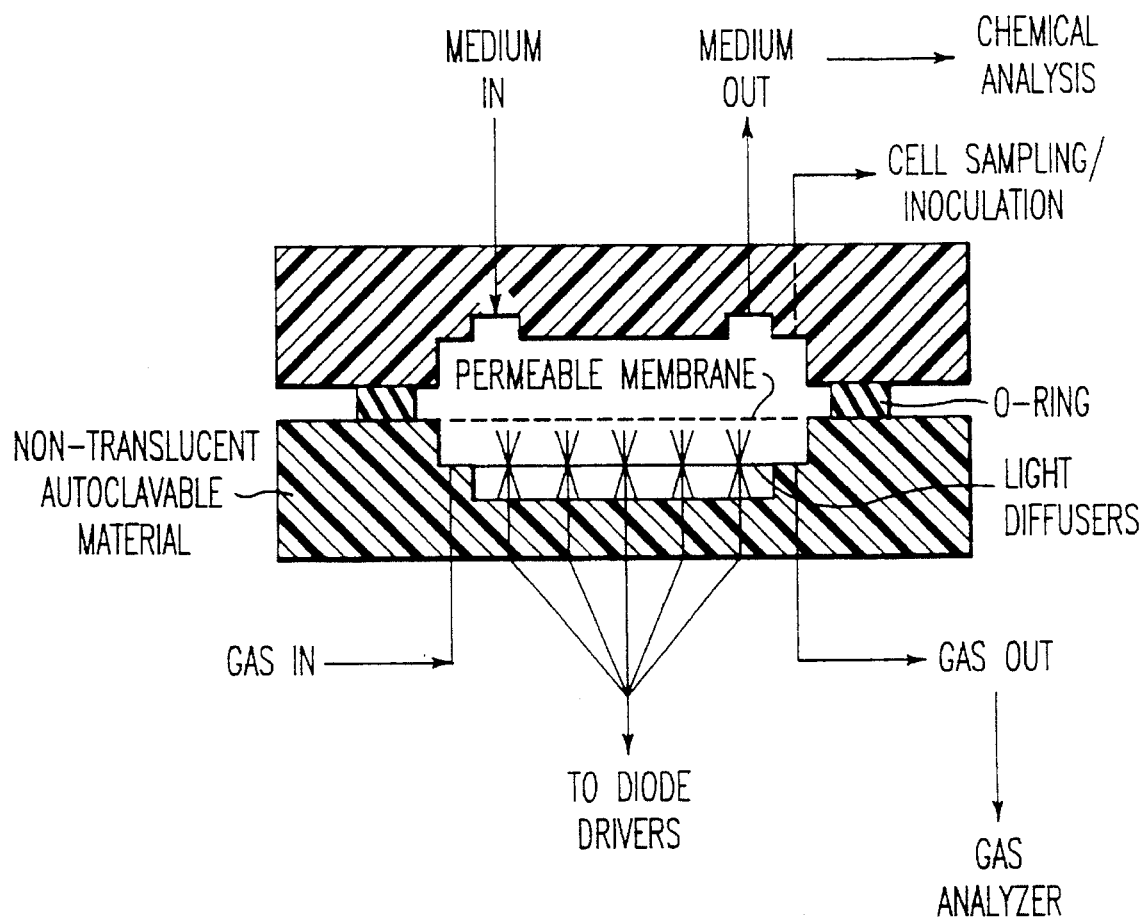
FIG. 12 schematically represents an embodiment of a perfusion chamber utilized in one embodiment of the present artificial lung.

FIG. 12 shows a design of small illuminated perfusion chamber. The cells are located in the top portion of the chamber. Medium (consists of $Na_2HPO_4$, $KH_2PO_4$, $CaCl_2$, EDTA, $MgSO_4$, $KNO_3$, and trace elements such as iron, $Al_2(SO_4)_3$, $MnCl_2$, $CuSO_4$, and $ZnSO_4$) can be perfused at an appropriate rate through the top portion through the membrane sealed ports that prevent the algal cells from leaving the chamber. The cell sample and inoculation port also enters the top compartment. Through the port, cells can be removed periodically for counting, determination of chlorophyll content, cell cycle analysis and other assays. The chamber can also be run in a continuous mode with continuous removal of cells through the cell sampling port. The upper chamber is separated from the lower by a gas permeable membrane (silicone, goretex, etc). Gases circulate through the lower portion and are exchanged with the culture medium across the gas exchange membrane. The gas composition (nitrogen, oxygen, carbon dioxide) can be specified and controlled. The light source may be located at the bottom of the lower chamber behind a suitable light diffusing membrane. The light can be provided from a number of different light sources as described below. The circuit board and power requirements (in the case of light emitting diodes) or an optic fiber transmission system (in the case of a laser or broad band source) may be interfaced at the bottom of the chamber.

Delivery of Defined Light

A filtering system that allows for the delivery of defined spectra, which allows a precise study of how the frequency composition influences the biological behavior of the algal cells, may be used. Alternatively, gas or solid state laser sources to illuminate the reaction fluid may be used. A high-powered laser assembly including an argon laser radiating in the blue region, or normally 458 nm, and a Helium-Neon laser radiating in the red region, or normally 633 nm can be directly substituted for a high intensity light source. Lasers of this type can conveniently provide about 10 mW of optical power with nominal inputs of 60 watts. While this light generation efficiency is similar to that in an arc lamp-type system, all the light energy is collimated, and generated at the frequencies of interest for plant metabolism.

Electro-Optically Illuminated Surfaces

Figure 13A:
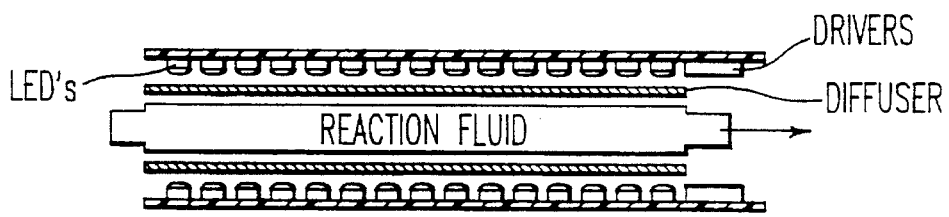
FIG. 13a, 13b and 13c schematically illustrate an electro-optical light delivery system to suspension cultures. (A) A light emitting diodes (LED) illuminated reactor sandwich. The dark area represents reaction fluid. (B) A LED array on flexible circuit board. (C) A LED illuminator driver system.

To make more compact and practical systems, it may be advantageous to utilize of the size of semiconductor devices to fabricate flexible light sheet devices. FIGS. 13*a*, 13*a*, and 13*c* a reactor sandwich, using an illumination sheet. This configuration can be made by mounting a two dimensional array of light emitting diodes on a rigid or flexible mylar circuit board (readily available commercially), along with drive/multiplexing electronics, FIGS. 13a, 13a, and 13c and (optional) diffusion panel.

This arrangement has several advantages: (i) low cost 10–30 mW red light emitting diodes are available at 10 to 70 cents per diode; (ii) blue diodes of comparable power are available in the 10 to 15 dollar range; (iii) the flexible mylar board allows the same basic illuminator design to be used for a variety of alternative reactor shapes; (iv) the low power requirement of each diode and therefore the simplicity of the drive electronics supports very flexible pulsing and modulation sequence programming (from external computer). Permutation and oscillatory delivery of light (the circuit can be designed so that the light emitting diodes are switched off and on at high frequency, faster than a microsecond) may be utilized.

Alternatively, a full spectrum source and an optic fiber transmission system may be used. Filters can be used to help define which bands of light are necessary for growth.

In Vitro Test Circuit

Figure 14:
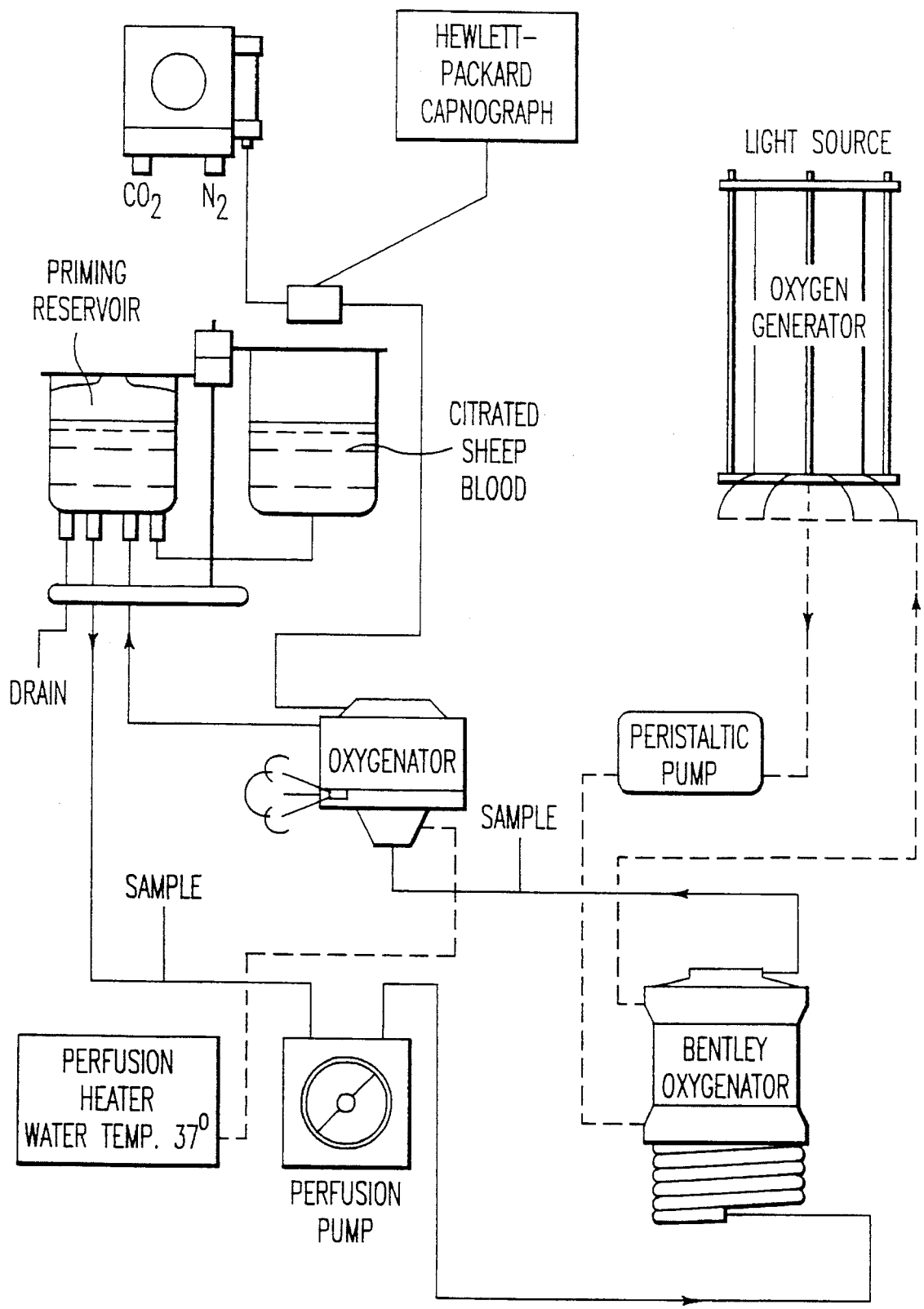
FIG. 14 illustrates an embodiment of the present artificial lung. The Medtronic oxygenator serves as a deoxygenator (metabolitzer). In the ex vivo setup, part "A" and the metabolizer are replaced by the animal.

A schematic diagram of an in vitro experimental setup is shown in FIG. 14. Fresh sheep blood may be pumped in and out of an airless and debubbled SciMed Pediatric Priming Reservoir and normalized by a Medtronic Maxima oxygenator. The Maxima oxygenator may be used as a metabolizer or deoxygenator which may be controlled to achieve the $CO_2$ production and oxygen consumption of the in vivo model. The blood may be circulated through the blood phase of a membrane test lung (i.e. the Bentley oxygenator in FIG. 14), whereas the algal suspension may be circulated from the oxygen generator through the gas phase of the membrane test lung. The flow rate of the algal suspension through the membrane lung may be varied between 100–1000 cc/min. The two sampling sites permit measurements of $PO_2$, $PCO_2$, and pH in the blood circulating through the test membrane lung. The $PO_2$ of the algal suspension may also be evaluated under a variety of conditions. The effect of variable levels of $PO_2$ on the gas transfer may be measured. Of particular importance is the effect of the $PO_2$ gradient on actual oxygen transfer. In addition, the effect of variable $PCO_2$ on reaction rate of the algal suspension may be evaluated and the gradient required for $CO_2$ transfer may be determined.

Venous Blood Source

A large Metronic oxygenator may be used as a deoxygenator. It may be ventilated with 5% $CO_2$ and 95% $N_2$ to simulate venous blood conditions. The $CO_2$ may be analyzed by continuous infrared capnography using a Hewlett-Packard $CO_2$ monitor. Deoxygenated (venous) blood may be circulated with a small roller pump to the membrane test lung. Blood flow rate may range from 100–1000 cc/min.

Membrane Lung

Two commercially available oxygenation devices may be used: the Medtronic Maxima oxygenator and the SciMed oxygenator. The Maxima is a conventional blood outside capillary membrane lung which has a priming volume of 300 ml and a rated flow of 5 liters per minute. In this device the venous blood and the algal solution will not be in direct contact, but gas exchange will take place through the microporous walls of the hollow fibers. By testing for blood and serum albumin in the algae solution it is possible to determine the leak rate, if any, between blood and algae. Pressure on the blood side may be maintained higher than the pressure on the algal side, using a DLP pressure monitor system. This is a system currently used in clinical ECMO cases to monitor flow/pressure changes in the oxygenators.

The SciMed is a solid silicon rubber membrane lung. Therefore, there is no leakage between the blood and the algal suspension.

Blood Source and Characteristics

Two liters of fresh sheep blood may be utilized for each experiment. This blood volume is about equal to that of the testing animal. The blood may be anticoagulated with heparin, and may be circulated in the deoxygenator system equilibrated with 5% $CO_2$, 85% $N_2$, and 10% $O_2$ until blood gas measurements demonstrate nominal venous blood characteristics. It has been found that a steady flow of normal venous blood can be produced for periods up to 24 hours without deterioration. By regulating the gas flow and composition, a variety of venous blood characteristics can be simulated. Using the large blood deoxygenator to create venous blood characteristics, the gas exchange between the bioreactor fluid and venous blood can be evaluated under a wide variety of test conditions.

Gas Exchange Measurements venous blood may be circulated through the test membrane lung with a roller pump. The flow rate and inlet and outlet blood gases may be measured. Oxygen content may be calculated and oxygen consumption calculated in turn as arterial venous oxygen difference times blood flow. Carbon dioxide content may be calculated based on $PCO_2$ and carbon dioxide transfer may be calculated as arterial venous difference for $CO_2$ content times flow.

The Ex Vivo Circuit

The setup for the ex vivo apparatus is similar to that shown in FIG. 14, with the animal replacing the priming reservoir and the metabolizer (i.e. the deoxygenator).

A continuous infusion of heparin may be given in a dose sufficient to maintain the whole blood activated clotting time between 180–200 seconds. This is the standard regimen for anticoagulation for patients on prolonged extracorporeal circulation. The patient may be anesthetized and cannulated for extracorporeal circulation. Venous blood from the right atrium may be drained by gravity, pumped through the membrane test lung, and returned to the arterial circulation. The algae solution may be circulated from the bioreactar (i.e. the oxygen generator) via plastic tubing and a small pump through the gas phase of the membrane test lung, through a dialysis unit which allows for the removal of inhibitory substances that may build up in the culture medium and then return to the bioreactor. Carbon dioxide required for the algae oxygen generator may initially be provided from both the animal's venous blood and an external source. Once carbonic anhydrase is successfully immobilized on the membrane test lung, carbon dioxide is expected to be fully supplied by the flowing blood.

Gas Exchange Measurements

Arterial and venous $O_2$ and $CO_2$ content may be measured and actual gas transfer may be calculated. Gas exchange and pressure flow characteristics may be measured over a wide range of blood flow rates and venous blood characteristics.

Surface Coatings

Materials may be coated on the surface of the membrane of the lung.

Surface coatings of heparin, thrombolytic enzymes (e.g. urokinase), and stable prostagladin analogs (e.g. prostacyclin) on the test membrane lung (on the blood site) and on the PVC tubing which is used extensively in the extracorporeal circuit, are advantageous.

Coating on the Membrane Lungs

The SciMed membrane lung is made of silicon rubbers. Silicon rubbers are very inert materials and thus very difficult to have agents attached to them through direct covalent linkages. They can, however, be prepared to contain functional groups suitable for agent immobilization by tailoring the surface with silanes containing these functional groups. A detailed review of the available tailoring methods is made by Arkles (Arkles B: Tailoring surfaces with silanes. CHEMTECH, December, pp 766–778, 1977). The tailoring method described by Messings et al. (Messing R A, Horseheads, Weetall H H: Chemically coupled enzymes. U.S. Pat. No. 3,519,538, 1970) is also adequate. Described below is a brief summary regarding how to incorporate functional groups to the silicon rubber-made/coated oxygenator surface. A solution containing 10% γ--aminopropyltriethyloxysilane in toluene may be passed through the blood phase of the oxygenator over a period of two hours. The treated surface may be washed with acetone and air dried. Since the silane-treated surface contains free amino groups, the aforementioned/agents can be attached to it through either covalent or ionic linkages.

The Medtronic Maxima membrane lung is made of polypropylene. Polypropylene can be modified to contain the free amino functional groups, using the same "silane-tailoring" coating method described above. The advantage of coating the polypropylene surface with a thin film of silane lies in silane's proven excellence in gas exchange (Arkles B: Tailoring surfaces with silanes. CHEMTECH, December, pp 766–778, 1977). The IVOX oxygenation device is made of microporous fibers coated with a very thin layer of silicon rubber.

Heparin

Ionically bound heparin is more active than covalently bound heparin with regard to the anticoagulant activity (Holland F F,Gidden H E, Mason R G, Klein E: Thrombogenicity of heparin-bound DEAE cellulose hemodialysis membranes, *Trans. Am. Soc. Artif. Intern. Organs* 24: 24–36, 1978; Larm O, Larsson R, Olsson P: A new nonthrombogenic surface by selective covalent binding of heparin via a modified reducing terminal residue, Biomat. Med. Dev. Art. Org. 11: 161–173, 1983). Since heparin is an acidic molecule, it can be directly adsorbed to the aminated membrane surface through electrostatic interaction. The amount of heparin adsorbed on the oxygenator may be determined by measuring the heparin concentration in the solution before and after the immobilization. The heparin cocentration may be determined by the Azure A assay (Jaques L B, Wollin A: A modified method for the colorimetric determination of heparin, *Can. J. Physiol. Pharmacol* 45: 787–794, 1967).

Thrombolytic Enzymes

Urokinase may be immobilized on the silane-treated membrane surface via a covalent linkage. The enzyme solution may be added to a mixture (1:1; v/v) of N',N'-dicyclohexyl-carbodiimide (DCCI) in tetrahydrofuran. Immediately after mixing, the solution may be perfused through the blood phase (i.e. the treated phase) of the oxygenator over a period of two hours. The amount of urokinase immobilized on the oxygenator may be determined by measuring the urokinase activity in the solution before and after the immobilization. Urokinase activity may be determined according to the procedure described previously (Olshiro T, Liu M C, Kambayashi J, Mori T: Clinical applications of urokinase-treated material, *Methods Enzymol.* 137: 529–545, 1988).

Prostacyclin

Prostacyclin has been shown to stimulate the membrane adenylate cyclase, increasing the cyclic AMP level within the platelet and inhibit platelet aggregation (Gorman RR: Modulation of human platelet function by prostacyclin and thromboxane $A_2$, *Fed. Proc.* 38: 83–88, 1979). Since the functional group on the prostacyclin molecule that is involved in the inhibition is not known yet, the molecule may be attached to the oxygenator through ionic immobilization. Due to the acidic nature of prostacyclin, it can be directly immobilized onto the silane-treated oxygenator by electrostatic interaction.

A variety of other surface-modification techniques (Ward W J, McCarthy T J: Surface modification, in: *Encyclopedia of Polymer Science & Engineering*, 2nd ed., pp 674–689, 1989) such as that of plasma modification of silicon rubber by Hudis and Prescott (Hudis M, Prescott L E: *J. Appl. Polym. Sci.* 19: 451–462, 1976) may be used.

Coating on Polyvinyl Chloride (PVC) Surfaces

Polyvinyl chloride membranes containing immobilized agents have been widely documented and used to prepare membrane sensors (Ma S C, Meyerhoff M E: Potentiometric pH response of membrane prepared with various aminated-poly(vinyl chloride) products, *Mikrochim. Acta* 1: 197–208, 1990; Kihara K, Yasukawa E, Hayashi M, Hirose S: Determation of glutamate-pyruvate transaminase activity in blood serum with a pyruvate oxidase/poly(vinyl chloride) membrane sensor, *Analytica Chimica Acta* 159: 81–86, 1984; Alexander P W, Joseph J P: A coated-metal enzyme electrode for urea determinations, *Analytica Chimica Acta* 131: 103–109, 1981).

Heparin

Heparin may be ionically attached to an aminated PVC surface. The PVC tubing may be briefly treated with tetrafuran solution containing solubilized alkyl quaternary amines. Immediately after the treatment, the tubing may be quickly air dried so that the hydrophobic (i.e. the alkyl) group of the quaternary amine will be impregnated into the PVC hydrophobic matrix whereas the polar, hydrophobic amine group will be pointing away from the PVC membrane. The acidic heparin may then be adsorbed onto the aminated PVC surface via the electrostatic interaction.

Thrombolytic Enzymes

Urokinase may be immobilized onto the PVC tubing according to the method described by Ohshiro. PVC tubing may first be treated with 15% NaOH-methanol at 60° C. for 2 hours. After the saponification step, the tubing may be further treated with 2% aminoacetaldehyde-diethylacetal-HCl at 58° C. for 5 hours, followed by the treatment with 4% maleic anhydride-methyl vinyl ether copolymer (Gantrez) in acetone. A urokinase solution may then be passed through the activated PVC tubing to allow the enzyme to be linked to the inner surface of the tubing via Gantrez. Results show that urokinase thus immobilized is stable and maintains more than 60% of its fibrinolytic activity (Olshiro T, Liu M C, Kambayashi J, Mori T: Clinical applications of urokinase-treated material, *Methods Enzymol.* 137: 529–545, 1988).

Prostacyclin

Prostacyclin can be immobilized onto the aminated PVC tubing according to the procedures described above.

Should the preparation of a thrombo resistant circuit require coating of above agents onto other materials, a number of surface modification can bemused (Ward W J, McCarthy T J: Surface modification, in: *Encyclopedia of Polymer Science & Engineering*, 2nd ed., pp 674–689, 1989; *Methods in Enzymology* (Mosback K, Ed.), vol. 137, Academic Press, New York, 1988). A variety of labile agents including enzymes (e.g. heparinase), proteins (e.g. protamine), polyelectrolytes (e.g. polyamines and heparin), and small ions (e.g. DEAE) have been immobilized onto a number of different biomaterials including agarose beads, hollow fibers, and polyvinyl chloride membrane.

Testing of the Thrombogenecity of the Coated Materials

Each of the above coated oxygenator may be connected with its PVC counterpart for testing. Thrombogenecity may be evaluated using a chronic awake sheep thrombosis evaluation system (Toomasian J M, Hsu L C, Hirschl R B, Hultquist K A: Evaluation of Duraflo II heparin coating in prolonged extracorporeal membrane oxygenation, *Trans. Am. Soc. Artif. Intern. Organs* 34: 410–414, 1988; Toomasian J M, Zwischenberger J B, Oram A D, DeSmet G M, Bartlett R H: The use of bound heparin in prolonged extracorporeal membrane oxygenation, *Trans. Am. Soc, Artif. Intern. Organs* 30: 133–136, 1984; Bartlett R H, Fong S W, Burns N E, Gazzaniga A B: Prolonged partial venoarterial bypass: Physiologic, biochemical and hematologic response, *Ann. Surg.* 180: 850–856, 1974). Venovenous bypass from the jugular to the femoral vein may be used for thrombosis and/or anticoagulation testing so that any thrombolli will lodge in the pulmonary vascular bed. These studies may be conducted with conventional membrane lungs with gas in the gas phase to determine the applicability of the three component surface to routine clinical extracorporeal circulation. The size of the sheep is chosen to permit extracorporeal flow above the rated flow of the membrane lung in the circuit. The maintenance flow rate is approximately ½ of rated flow to provide flow patterns and thrombogenesis which might be encountered in clinical extracorporeal circulation with that circuit. Experiments may be maintained for two to four days. The sheep is quick to thrombose and slow to lyse so that a device or technique which is successful in the chronic sheep is routinely successful in the human.

Coatings to Enhance $CO_2$ Transfer

The $CO_2$ content of whole blood is three times higher than the oxygen content (Kleiber M *The Fire of Life*, 3rd ed., Robert Krieger Company, Malabor Fla., 1987; Nolte SH, Jonitz W J, Grau J, Roth H, Assenbaum E R: Hemodialysis for extracorporeal bicarbonate/$CO_2$ removal (ECBicCO2R) and apneic oxygenation for respiratory failure in the newborn. Theory and preliminary results in animal experiments, *Trans. Am. Soc. Artif. Intern, Organs* 35: 30–34, 1989). At normal blood pH, only a small part of $CO_2$ (about 5%) is available as free $CO_2$, while the most of it is bound as bicarbonate (Nolte S H, Jonitz W J, Grau J, Roth H, Assenbaum E R: Hemodialysis for extracorporeal bicarbonate/$CO_2$removal (ECBicCO2R) and apneic oxygenation for respiratory failure in the newborn. Theory and preliminary results in animal experiments, *Trans. Am. Soc. Artif. Intern. Organs* 35: 30–34, 1989). Because of the resistance of the gas exchange membrane to ions (e.g. bicarbonate), it has been suggested to combine ECMO with a hemodialysis procedure to enhance $CO_2$ removal (Kolobow T, Gattinoni L, Tomlinson T, Pierce J E: An alternative to breathing, *J, Thorac. Cardiovasc. Surg.* 75: 261–266, 1978; Kolobow T, Fumagalli R, Arosio P, Chen V, Buckhold D K, Pierce J E: The use of the extracorporeal membrane lung in the successful resuscitation of severely hypoxyxic and hypercapnic fetal lamb, *Trans. Am. Soc. Artif. Intern. Organs* 28: 365–368, 1982). Kolobow and coworkers have demonstrated that even in severely damaged lungs, sufficient oxygenation and gas exchange can be maintained only by removing $CO_2$ extracorporeally (Kolobow T, Gattinoni L, Tomlinson T, Pierce J E: An alternative to breathing, *J. Thorac. Cardiovasc. Surg.* 75: 261–266, 1978). Thus, carbonic anhydrase, an enzyme in the erythrocyte which catalyzes the conversion of bicarbonate to free $CO_2$, onto the blood phase of the oxygenator membrane, should be immobilized. The carbonic anhydrase would convert biocarbonate in the blood to $CO_2$, which will then diffuse through the gas exchange membrane and convert back to the bicarbonate form in the algal phase. The significance of this approach is manifold: (i) it provides extra $CO_2$ removal and, as described above, enhances oxygenation and gas exchange between the blood and the algal phase; (ii) oxygenation and gas exchange are achieved at lower algae flow rates; and (iii) it provides suffcient $CO_2$ to the algae, which is the main nutrition for their growth.

Toxicology Studies

The silicon rubber-made/coated membrane in the oxygenator is designed primarily for only gas exchange. Unless there are ruptured capillaries, blood cells and algae are not expected to cross the membrane. There is, however, still present the possibility that components in the algae phase may gain access to the blood phase and vice versa. The former may result in toxic effects on the patient, whereas the latter may result in toxic effects on algal growth.

Toxicity of Plasma Ingredients on Algae

The toxic effect of plasma ingredients on algal growth may be evaluated by adding different volume of plasma to an already growing algal culture. The DNA histogram, determined by cytometry at various growth time may be used as the toxicity parameter. A new and novel algal assay, which is developed recently by Dr. Knie and his colleages at the Landesamt Fur Wasser und Abfall in Germany, may also be used to measure the effect of plasma on algae. The test is of short duration (less than 20 minutes) and is a procedure in which measured oxygen and fluorescence decreases serve as a function of potential toxicity (Personal communication with Dr. Joachim Knie at the Landesamt fur Wasser und Abfall, Nordrhein-Westfalen, auf dem Draap 25, D-4000 Dusseldorg 1, Germany).

Obviously, numerous modifications and variations of the present invention are possible in light of the above teachings. It is therefore to be understood that, within the scope of the appended claims, the invention may be practiced otherwise than as specifically described herein.

We claim:

1. A method for producing a biologically-active compound, comprising:

(i) culturing cells capable of producing said biologically-active compound in a photobioreactor comprising a hollow, cylindrical irradiation chamber, wherein said chamber comprises a top sealed to a cylindrical side wall; a bottom sealed to said cylindrical side wall; said top, bottom and cylindrical side wall together enclosing a cylindrical space; a first cylindrical light irradiator disposed in said cylindrical space and attached only to said top; and a second cylindrical light irradiator disposed in said cylindrical space and attached only to said bottom; wherein all cylindrical light irradiators and said cylindrical side wall are coaxial; the distance between said cylindrical side wall and cylindrical light irradiator closest to said side wall is within 1 mm to 20 cm, and the distance between each adjacent cylindrical light irradiator is within 1 mm to 20 cm, for a time sufficient to produce said biologically-active compound, while irradiating said cells with said first light cylindrical irradiator and said second light cylindrical irradiator.

2. The method of claim 1, wherein said light irradiator comprises light emitting diodes.

3. The method of claim 1, wherein said photobioreactor further comprises an outlet at the center of said top and an inlet in said sidewall.

4. The method of claim 3, wherein said photobioreactor further comprises an ultrafiltration unit connected to said outlet.

5. The method of claim 1, wherein said biologically-active compound is a secondary metabolite or a secreted product.

6. The method of claim 1, wherein said biologically active compound is a protein, growth factor, antibiotic, antitumor active compound, vitamin, organic acid, polysaccharide, or pigment.

7. The method of claim 1, wherein said cells are photoautotrophic cells.

8. The method of claim 7, wherein said cells are selected from the group consisting of Chlorella, Scenedesmus, Chlamydomonas, and Cyanobactera.

9. A photobioreactor, comprising a hollow, cylindrical irradiation chamber, wherein said chamber comprises a top sealed to a cylindrical side wall; a bottom sealed to said cylindrical side wall; said top, bottom and cylindrical side wall together enclosing a cylindrical space; a first cylindrical light irradiator disposed in said cylindrical space and attached only to said top; and a second cylindrical light irradiator disposed in said cylindrical space and attached only to said bottom; wherein all cylindrical light irradiators and said cylindrical side wall are coaxial; the distance between said cylindrical side wall and cylindrical light irradiator closest to said side wall is within 1 mm to 20 cm, and the distance between each adjacent cylindrical light irradiator is within 1 mm to 20 cm.

10. The photobioreactor of claim 9, wherein said light irradiators comprise light emitting diodes.

11. The photobioreactor of claim 9, further comprising an outlet at the center of said top and an inlet in said sidewall.

12. The photobioreactor of claim 11, further comprising an ultrafiltration unit connected to said outlet.

13. In a closed ecological life support system, comprising a photobioreactor, the improvement being said photobioreactor comprises a hollow, cylindrical irradiation chamber, wherein said chamber comprises a top sealed to a cylindrical side wall; a bottom sealed to said cylindrical side wall; said top, bottom and cylindrical side wall together enclosing a cylindrical space; a first cylindrical light irradiator disposed in said cylindrical space and attached only to said top; and a second cylindrical light irradiator disposed in said cylindrical space and attached only to said bottom; wherein all cylindrical light irradiators and said cylindrical side wall are coaxial; the distance between said cylindrical side wall and cylindrical light irradiator closest to said side wall is within 1 mm to 20 cm, and the distance between each adjacent cylindrical light irradiator is within 1 mm to 20 cm.

14. The closed ecological life support system of claim 13, wherein said light irradiators comprise light emitting diodes.

15. The closed ecological life support system of claim 13, wherein said photobioreactor further comprises an outlet at the center of said top and an inlet in said sidewall.

16. The closed ecological life support system of claim 15, wherein said photobioreactor further comprises an ultrafiltration unit connected to said outlet.

17. An artificial lung, comprising:

(i) a means for converting $CO_2$ from a patient's blood stream to oxygen; and (ii) a means for exchanging said oxygen with said $CO_2$ between said patient's blood stream and said means of converting, wherein said means for converting comprises a hollow, cylindrical irradiation chamber, wherein said chamber comprises a top sealed to a cylindrical side wall; a bottom sealed to said cylindrical side wall; said top, bottom and cylindrical side wall together enclosing a cylindrical space; a first cylindrical light irradiator disposed in said cylindrical space and attached only to said top; and a second cylindrical light irradiator disposed in said cylindrical space and attached only to said bottom; wherein all cylindrical light irradiators and said cylindrical side wall are coaxial; the distance between said cylindrical side wall and cylindrical light irradiator closest to said side wall is within 1 mm to 20 cm, and the distance between each adjacent cylindrical light irradiator is within 1 mm to 20 cm.

18. The artificial lung of claim 17, wherein said light irradiators comprise light emitting diodes.

19. The artificial lung of claim 17, wherein said means for converting further comprises an outlet at the center of said top and an inlet in said sidewall.

20. The artificial lung of claim 19, wherein said means for converting further comprises an ultrafiltration unit connected to said outlet.

* * * * *

UNITED STATES PATENT AND TRADEMARK OFFICE
CERTIFICATE OF CORRECTION

PATENT NO. : 5,614,378
DATED : MARCH 25, 1997
INVENTOR(S) : YANG ET AL

It is certified that error appears in the above-identified patent and that said Letters patent is hereby corrected as shown below:

Column 3, line 27, "to well a established" should read --to a well established--.

Column 9, line 30, "to 700 run" should read --to 700 nm--.

Column 10, line 41, "preferably 0.3 to 0.5" should read --preferably 0.03 to 0.05--.

Column 11, line 38, "*Chlorella vulgares,*" should read --*Chlorella vulgaris,*--.

Column 14, line 55, "$4 \times 10^8$ cells/m ," should read --$4 \times 10^8$ cells/ml,--.

Column 15, line 62, "achieve the optinum" should read --achieve the optimum--.

Column 16, line 51, "*Serenastrum*" should read --*Selenastrum*--.

Column 18, line 64, "to utilize of the size" should read --to utilize the size--.

UNITED STATES PATENT AND TRADEMARK OFFICE
CERTIFICATE OF CORRECTION

PATENT NO. : 5,614,378
DATED: : MARCH 25, 1997
INVENTOR(S) : YANG ET AL

Figure 13B:
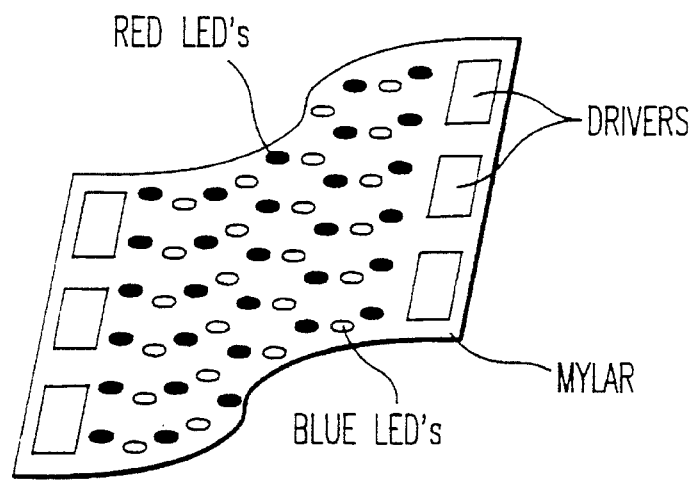
Figure 13C:
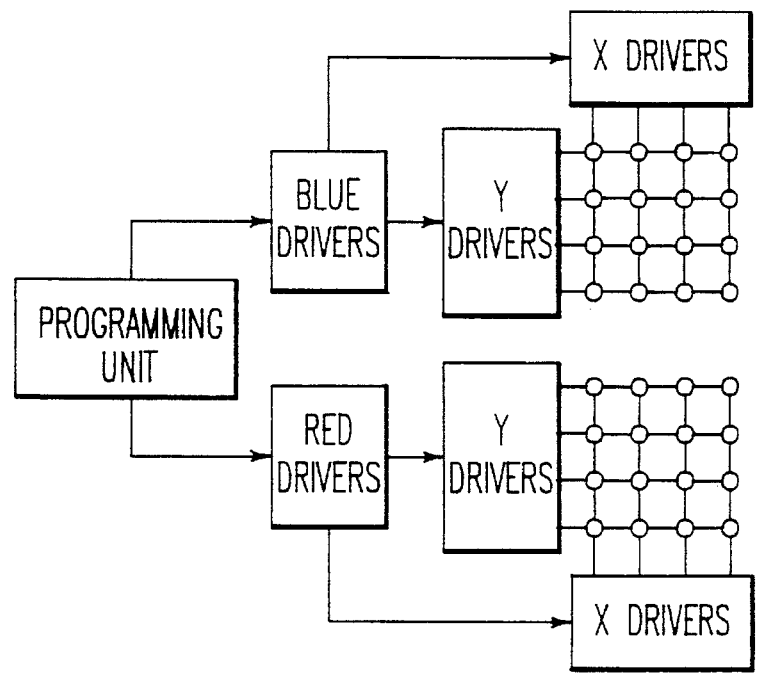

It is certified that error appears in the above-identified patent and that said Letters patent is hereby corrected as shown below:

Column 18, lines 65-66, "FIGS. 13a, 13a, and 13c a reactor" should read --FIGS. 13a, 13b, and 13c, show a reactor--.

Column 19, line 3, "FIGS. 13a, 13a, and 13c" should read --FIGS. 13a, 13b, and 13c--.

Column 20, line 17, "venous blood" should read --Venous blood--.

Column 21, line 14, "mentioned/agents can" should read --mentioned agents can--.

UNITED STATES PATENT AND TRADEMARK OFFICE
CERTIFICATE OF CORRECTION

PATENT NO. : 5,614,378
DATED: : MARCH 25, 1997
INVENTOR(S) : YANG ET AL

It is certified that error appears in the above-identified patent and that said Letters patent is hereby corrected as shown below:

Column 22, line 55, "can bemused" should read --can be used--.

Column 23, line 39, "while the most of it" should read --while most of it"--.

Column 23, line 49, "breathing, $J$," should read --breathing, $J$.--.

Signed and Sealed this

Thirtieth Day of June, 1998

BRUCE LEHMAN

*Attesting Officer*    *Commissioner of Patents and Trademarks*